(12) United States Patent
Windeballe et al.

(10) Patent No.: US 12,310,877 B2
(45) Date of Patent: May 27, 2025

(54) SENSOR PATCH FOR AN OSTOMY APPLIANCE

(71) Applicant: Coloplast A/S, Humlebaek (DK)

(72) Inventors: Lars Stendevad Windeballe, Virum (DK); Stephanie Knoedler, Nivaa (DK)

(73) Assignee: Coloplast A/S, Humlebaek (DK)

( * ) Notice: Subject to any disclaimer, the term of this patent is extended or adjusted under 35 U.S.C. 154(b) by 724 days.

(21) Appl. No.: 17/424,896

(22) PCT Filed: Jan. 30, 2020

(86) PCT No.: PCT/DK2020/050028
§ 371 (c)(1),
(2) Date: Jul. 22, 2021

(87) PCT Pub. No.: WO2020/156626
PCT Pub. Date: Aug. 6, 2020

(65) Prior Publication Data
US 2022/0079803 A1  Mar. 17, 2022

(30) Foreign Application Priority Data

Jan. 31, 2019 (DK) .......................... PA 2019 70071

(51) Int. Cl.
*A61F 5/44* (2006.01)
*A61F 5/443* (2006.01)
(52) U.S. Cl.
CPC ............ *A61F 5/4404* (2013.01); *A61F 5/443* (2013.01)

(58) Field of Classification Search
CPC ......... A61F 5/4404; A61F 5/443; A61F 5/445
See application file for complete search history.

(56) References Cited

U.S. PATENT DOCUMENTS

| 2,327,514 A | 8/1943 | Fenwick |
| 2,542,233 A | 2/1951 | Carroll |
| 2,544,579 A | 3/1951 | Ardner |
| 3,214,502 A | 10/1965 | Schaar |
| 3,808,354 A | 4/1974 | Feezor et al. |

(Continued)

FOREIGN PATENT DOCUMENTS

| AU | 2007342523 B2 | 7/2011 |
| CA | 2540756 C | 1/2008 |

(Continued)

*Primary Examiner* — Susan S Su
*Assistant Examiner* — Ted Yang
(74) *Attorney, Agent, or Firm* — Coloplast Corp., Coloplast A/S; Nick Baumann

(57) ABSTRACT

A sensor patch (100) for attachment to a base plate of an ostomy appliance is provided. The sensor patch comprises a distal surface, a proximal surface, and an outer contour. The distal surface is adapted for attachment to an adhesive surface of the base plate, and the proximal surface being adapted for attachment to the skin surface of a user. The sensor patch further comprises one or more electrodes (102a, 102b) comprising a spatial layout, and a planar adhesive layer (110) having a proximal side and a distal side (110b) and comprising a first spatial shape. The one or more electrodes are arranged on the distal side of the adhesive layer and the first spatial shape of the adhesive layer generally corresponds to the spatial layout of the one or more electrodes.

20 Claims, 16 Drawing Sheets

(56) References Cited

U.S. PATENT DOCUMENTS

| | | |
|---|---|---|
| 3,832,510 A | 8/1974 | Pfau et al. |
| 3,915,171 A | 10/1975 | Shermeta |
| 3,941,133 A | 3/1976 | Chen |
| 4,231,369 A | 11/1980 | Sorensen et al. |
| 4,372,308 A | 2/1983 | Steer et al. |
| 4,449,970 A | 5/1984 | Bevan et al. |
| 4,668,227 A | 5/1987 | Kay |
| 4,754,264 A | 6/1988 | Okada et al. |
| 4,775,374 A | 10/1988 | Cilento et al. |
| 4,834,731 A | 5/1989 | Nowak et al. |
| 4,973,323 A | 11/1990 | Kaczmarek et al. |
| 4,982,742 A | 1/1991 | Claude |
| 5,013,307 A | 5/1991 | Broida |
| 5,016,645 A | 5/1991 | Williams et al. |
| 5,051,259 A | 9/1991 | Olsen et al. |
| 5,074,851 A | 12/1991 | Plass et al. |
| 5,111,812 A | 5/1992 | Swanson et al. |
| 5,147,343 A | 9/1992 | Kellenberger |
| 5,237,995 A | 8/1993 | Cano |
| 5,318,543 A | 6/1994 | Ross et al. |
| 5,322,797 A | 6/1994 | Mallow et al. |
| 5,358,488 A | 10/1994 | Suriyapa |
| 5,486,158 A | 1/1996 | Samuelsen |
| 5,519,644 A | 5/1996 | Benton |
| 5,570,082 A | 10/1996 | Mahgerefteh et al. |
| 5,593,397 A | 1/1997 | La Gro |
| 5,626,135 A | 5/1997 | Sanfilippo |
| 5,672,163 A | 9/1997 | Ferreira et al. |
| 5,677,221 A | 10/1997 | Tseng |
| 5,704,905 A | 1/1998 | Jensen et al. |
| 5,714,225 A * | 2/1998 | Hansen .............. A61F 13/0246 428/114 |
| 5,790,036 A | 8/1998 | Fisher et al. |
| 5,800,415 A | 9/1998 | Olsen |
| 5,816,252 A | 10/1998 | Faries et al. |
| 5,834,009 A | 11/1998 | Sawers et al. |
| 5,846,558 A | 12/1998 | Nielsen et al. |
| 5,876,855 A | 3/1999 | Wong et al. |
| 5,879,292 A | 3/1999 | Sternberg et al. |
| 5,942,186 A | 8/1999 | Sanada et al. |
| 6,015,399 A | 1/2000 | Mracna et al. |
| 6,025,725 A | 2/2000 | Gershenfeld et al. |
| 6,078,261 A | 6/2000 | Davsko |
| 6,093,276 A | 7/2000 | Leise, Jr. et al. |
| 6,101,867 A | 8/2000 | Cavestri |
| 6,103,033 A | 8/2000 | Say et al. |
| 6,135,986 A | 10/2000 | Leisner et al. |
| 6,171,289 B1 * | 1/2001 | Millot .................... A61F 5/443 604/336 |
| 6,206,864 B1 | 3/2001 | Kavanagh et al. |
| 6,241,704 B1 | 6/2001 | Peterson et al. |
| 6,270,445 B1 | 8/2001 | Dean, Jr. et al. |
| 6,407,308 B1 | 6/2002 | Roe et al. |
| 6,433,244 B1 | 8/2002 | Roe et al. |
| 6,433,695 B1 | 8/2002 | Kai et al. |
| 6,482,491 B1 | 11/2002 | Samuelsen et al. |
| 6,485,476 B1 | 11/2002 | Von et al. |
| 6,520,943 B1 | 2/2003 | Wagner |
| 6,677,859 B1 | 1/2004 | Bensen |
| 6,764,474 B2 | 7/2004 | Nielsen et al. |
| 6,774,800 B2 | 8/2004 | Friedman et al. |
| 7,014,816 B2 | 3/2006 | Miller et al. |
| 7,066,919 B1 | 6/2006 | Sauerland et al. |
| 7,150,728 B2 | 12/2006 | Hansen et al. |
| 7,166,091 B1 | 1/2007 | Zeltner |
| 7,199,501 B2 | 4/2007 | Pei et al. |
| 7,214,217 B2 | 5/2007 | Pedersen et al. |
| 7,326,190 B2 | 2/2008 | Botten |
| 7,341,578 B2 | 3/2008 | Bulow et al. |
| 7,347,844 B2 | 3/2008 | Cline et al. |
| 7,367,965 B2 | 5/2008 | Poulsen et al. |
| 7,559,922 B2 | 7/2009 | Botten |
| 7,625,362 B2 | 12/2009 | Boehringer et al. |
| 7,641,612 B1 | 1/2010 | McCall |
| 7,670,289 B1 | 3/2010 | McCall |
| 7,943,812 B2 | 5/2011 | Stroebeck et al. |
| 7,981,098 B2 | 7/2011 | Boehringer et al. |
| 8,061,360 B2 | 11/2011 | Locke et al. |
| 8,277,427 B2 | 10/2012 | Edvardsen et al. |
| 8,319,003 B2 | 11/2012 | Olsen et al. |
| 8,326,051 B1 | 12/2012 | Hobbs |
| 8,343,437 B2 | 1/2013 | Patel |
| 8,398,575 B1 | 3/2013 | McCall |
| 8,398,603 B2 * | 3/2013 | Thirstrup .............. A61B 5/746 602/41 |
| 8,399,732 B2 | 3/2013 | Oelund et al. |
| 8,409,158 B2 | 4/2013 | Edvardsen et al. |
| 8,439,883 B1 * | 5/2013 | Johnsen ................. A61F 5/448 604/338 |
| 8,449,471 B2 | 5/2013 | Tran |
| 8,500,718 B2 | 8/2013 | Locke et al. |
| 8,507,081 B2 * | 8/2013 | Strobech ............. A61F 13/0226 604/336 |
| 8,632,492 B2 | 1/2014 | Delegge |
| 8,680,991 B2 | 3/2014 | Tran |
| 8,684,982 B2 | 4/2014 | Nguyen-Demary et al. |
| 8,707,766 B2 | 4/2014 | Harris et al. |
| 8,740,865 B2 | 6/2014 | Krystek et al. |
| 8,795,257 B2 | 8/2014 | Coulthard et al. |
| 8,821,463 B2 | 9/2014 | Grum-Schwensen |
| 8,821,464 B2 | 9/2014 | Hanuka et al. |
| 8,975,465 B2 | 3/2015 | Hong et al. |
| 8,978,452 B2 | 3/2015 | Johnson et al. |
| 9,046,085 B2 | 6/2015 | Schoess et al. |
| 9,066,812 B2 | 6/2015 | Edvardsen et al. |
| 9,216,104 B2 | 12/2015 | Thirstrup et al. |
| 9,308,332 B2 | 4/2016 | Heppe |
| 9,322,797 B1 | 4/2016 | Lastinger et al. |
| 9,506,886 B1 | 11/2016 | Woodbury et al. |
| 9,566,383 B2 | 2/2017 | Yodfat et al. |
| 9,629,964 B2 | 4/2017 | Wuepper |
| 9,649,230 B1 | 5/2017 | Li |
| 9,675,267 B2 | 6/2017 | Laakkonen et al. |
| 9,693,908 B2 | 7/2017 | Eriksson et al. |
| 9,770,359 B2 | 9/2017 | Edvardsen et al. |
| 9,788,991 B2 | 10/2017 | Bird |
| 9,867,934 B2 | 1/2018 | Heppe |
| 9,928,341 B2 | 3/2018 | Angelides |
| 10,016,298 B2 * | 7/2018 | Thirstrup ................ A61F 13/42 |
| 10,022,277 B2 | 7/2018 | Heil et al. |
| D826,740 S | 8/2018 | Stevens et al. |
| 10,426,342 B2 | 10/2019 | Hresko et al. |
| 10,500,084 B2 | 12/2019 | Hansen et al. |
| 10,531,977 B2 | 1/2020 | Schoess et al. |
| 10,646,370 B2 | 5/2020 | Keleny et al. |
| 10,792,184 B2 | 10/2020 | Hvid et al. |
| 10,799,385 B2 | 10/2020 | Hansen et al. |
| 10,849,781 B2 | 12/2020 | Hansen et al. |
| 10,874,541 B2 | 12/2020 | Seres et al. |
| 10,987,243 B2 * | 4/2021 | Thirstrup .............. A61B 5/746 |
| 11,096,818 B2 * | 8/2021 | Thirstrup ................ A61F 13/02 |
| 11,135,084 B2 | 10/2021 | Seres et al. |
| 11,219,436 B2 | 1/2022 | Mayberg |
| 11,238,133 B2 | 2/2022 | Brewer et al. |
| 11,306,224 B2 | 4/2022 | Chatterjee et al. |
| 11,406,525 B2 | 8/2022 | Seres et al. |
| 11,471,318 B2 | 10/2022 | Hansen et al. |
| 11,612,512 B2 | 3/2023 | Hansen et al. |
| 11,903,728 B2 | 2/2024 | Svanegaard et al. |
| 12,064,369 B2 | 8/2024 | Hansen et al. |
| 2001/0041920 A1 | 11/2001 | Starkweather et al. |
| 2001/0051787 A1 | 12/2001 | Haller et al. |
| 2002/0013613 A1 | 1/2002 | Haller et al. |
| 2002/0019615 A1 | 2/2002 | Roe et al. |
| 2002/0109621 A1 | 8/2002 | Khair et al. |
| 2003/0132763 A1 | 7/2003 | Ellenz |
| 2003/0169032 A1 | 9/2003 | Minchole et al. |
| 2004/0006320 A1 | 1/2004 | Buglino et al. |
| 2004/0030305 A1 | 2/2004 | Sakamoto |
| 2004/0036484 A1 | 2/2004 | Tamai |
| 2004/0049145 A1 | 3/2004 | Flick |
| 2004/0078219 A1 * | 4/2004 | Kaylor ................... G16H 40/67 600/300 |

(56) References Cited

U.S. PATENT DOCUMENTS

| | | | |
|---|---|---|---|
| 2004/0100376 A1* | 5/2004 | Lye | A61B 5/411 600/300 |
| 2004/0106908 A1 | 6/2004 | Leise et al. | |
| 2004/0133175 A1 | 7/2004 | Hagedorn-Olsen | |
| 2004/0171999 A1 | 9/2004 | Andersen et al. | |
| 2004/0193122 A1 | 9/2004 | Cline et al. | |
| 2004/0193123 A1 | 9/2004 | Fenton | |
| 2004/0216833 A1 | 11/2004 | Fleming et al. | |
| 2005/0038325 A1 | 2/2005 | Moll | |
| 2005/0054997 A1 | 3/2005 | Buglino et al. | |
| 2005/0065488 A1* | 3/2005 | Elliott | A61F 5/445 604/361 |
| 2005/0070863 A1 | 3/2005 | Bulow et al. | |
| 2005/0085779 A1 | 4/2005 | Poulsen et al. | |
| 2005/0101841 A9 | 5/2005 | Kaylor et al. | |
| 2005/0240163 A1 | 10/2005 | Andersen | |
| 2005/0256545 A1 | 11/2005 | Koh et al. | |
| 2005/0261645 A1 | 11/2005 | Conrad et al. | |
| 2006/0015081 A1 | 1/2006 | Suzuki et al. | |
| 2006/0025727 A1 | 2/2006 | Boehringer et al. | |
| 2006/0052752 A1 | 3/2006 | McMichael | |
| 2006/0194324 A1 | 8/2006 | Faries et al. | |
| 2006/0271002 A1 | 11/2006 | Botten | |
| 2007/0035405 A1 | 2/2007 | Wada et al. | |
| 2007/0135782 A1 | 6/2007 | Bager et al. | |
| 2007/0185464 A1 | 8/2007 | Fattman et al. | |
| 2007/0203407 A1 | 8/2007 | Hoss et al. | |
| 2007/0204691 A1 | 9/2007 | Bogner et al. | |
| 2008/0004580 A1 | 1/2008 | Mullejans et al. | |
| 2008/0038536 A1 | 2/2008 | Strobech et al. | |
| 2008/0041792 A1 | 2/2008 | Crnkovich et al. | |
| 2008/0058740 A1 | 3/2008 | Sullivan et al. | |
| 2008/0061965 A1 | 3/2008 | Kuhns et al. | |
| 2008/0071214 A1 | 3/2008 | Locke et al. | |
| 2008/0075934 A1 | 3/2008 | Barlow et al. | |
| 2008/0091154 A1 | 4/2008 | Botten | |
| 2008/0140057 A1 | 6/2008 | Wood et al. | |
| 2008/0234641 A1 | 9/2008 | Locke et al. | |
| 2008/0255808 A1 | 10/2008 | Hayter | |
| 2008/0275327 A1 | 11/2008 | Faarbaek et al. | |
| 2008/0278337 A1 | 11/2008 | Huang et al. | |
| 2008/0300559 A1 | 12/2008 | Gustafson et al. | |
| 2008/0300578 A1 | 12/2008 | Freedman | |
| 2008/0306459 A1 | 12/2008 | Albrectsen | |
| 2009/0012501 A1 | 1/2009 | Boehringer et al. | |
| 2009/0118687 A1 | 5/2009 | Kristensen et al. | |
| 2009/0167286 A1 | 7/2009 | Naylor et al. | |
| 2009/0173935 A1 | 7/2009 | Cho et al. | |
| 2009/0227969 A1 | 9/2009 | Jaeb et al. | |
| 2009/0234916 A1 | 9/2009 | Cosentino et al. | |
| 2009/0247970 A1 | 10/2009 | Keleny et al. | |
| 2009/0264957 A1 | 10/2009 | Giftakis et al. | |
| 2010/0010460 A1 | 1/2010 | Butler | |
| 2010/0030167 A1* | 2/2010 | Thirstrup | A61F 5/4404 340/657 |
| 2010/0072271 A1 | 3/2010 | Thorstensson | |
| 2010/0106220 A1 | 4/2010 | Ecker et al. | |
| 2010/0114047 A1 | 5/2010 | Song et al. | |
| 2010/0191201 A1 | 7/2010 | Bach et al. | |
| 2010/0271212 A1 | 10/2010 | Page | |
| 2010/0311167 A1 | 12/2010 | Wood et al. | |
| 2011/0034890 A1 | 2/2011 | Stroebech et al. | |
| 2011/0071482 A1 | 3/2011 | Selevan | |
| 2011/0077497 A1 | 3/2011 | Oster et al. | |
| 2011/0130642 A1 | 6/2011 | Jaeb et al. | |
| 2011/0144470 A1 | 6/2011 | Mazar et al. | |
| 2011/0191044 A1 | 8/2011 | Stafford | |
| 2011/0245682 A1 | 10/2011 | Robinson et al. | |
| 2011/0246983 A1 | 10/2011 | Brunet et al. | |
| 2011/0257496 A1 | 10/2011 | Terashima et al. | |
| 2012/0013130 A1 | 1/2012 | Jung | |
| 2012/0089037 A1 | 4/2012 | Bishay et al. | |
| 2012/0143154 A1* | 6/2012 | Edvardsen | A61F 5/4404 604/336 |
| 2012/0143155 A1* | 6/2012 | Edvardsen | A61F 5/443 604/318 |
| 2012/0258302 A1 | 10/2012 | Hunt et al. | |
| 2012/0283678 A1 | 11/2012 | Nguyen-Demary et al. | |
| 2012/0304767 A1 | 12/2012 | Howard et al. | |
| 2012/0323086 A1 | 12/2012 | Hansen | |
| 2013/0018231 A1 | 1/2013 | Hong et al. | |
| 2013/0030167 A1 | 1/2013 | Wang et al. | |
| 2013/0030397 A1 | 1/2013 | Sabeti | |
| 2013/0060213 A1 | 3/2013 | Hanuka et al. | |
| 2013/0066285 A1 | 3/2013 | Locke et al. | |
| 2013/0072886 A1 | 3/2013 | Schertiger et al. | |
| 2013/0078912 A1 | 3/2013 | San Vicente et al. | |
| 2013/0086217 A1 | 4/2013 | Price et al. | |
| 2013/0102979 A1 | 4/2013 | Coulthard et al. | |
| 2013/0138065 A1 | 5/2013 | Buus | |
| 2013/0150769 A1 | 6/2013 | Heppe | |
| 2013/0165862 A1 | 6/2013 | Griffith et al. | |
| 2013/0192604 A1 | 8/2013 | Persson et al. | |
| 2013/0226116 A1 | 8/2013 | Edvardsen et al. | |
| 2013/0231620 A1* | 9/2013 | Thirstrup | A61F 5/445 604/344 |
| 2013/0254141 A1 | 9/2013 | Barda et al. | |
| 2013/0303867 A1 | 11/2013 | Elfstrom et al. | |
| 2013/0307570 A1 | 11/2013 | Bosaeus et al. | |
| 2013/0324952 A1 | 12/2013 | Krystek et al. | |
| 2013/0324955 A1 | 12/2013 | Wong et al. | |
| 2013/0332085 A1 | 12/2013 | Yang et al. | |
| 2014/0051946 A1 | 2/2014 | Arne et al. | |
| 2014/0128815 A1 | 5/2014 | Cabiri et al. | |
| 2014/0200426 A1 | 7/2014 | Taub et al. | |
| 2014/0200538 A1 | 7/2014 | Euliano et al. | |
| 2014/0236111 A1 | 8/2014 | Casado et al. | |
| 2014/0275854 A1 | 9/2014 | Venkatraman et al. | |
| 2014/0276501 A1 | 9/2014 | Cisko | |
| 2014/0288381 A1 | 9/2014 | Faarbaek et al. | |
| 2014/0309600 A1 | 10/2014 | Aceto et al. | |
| 2014/0323909 A1 | 10/2014 | Kim | |
| 2014/0327433 A1 | 11/2014 | Anway et al. | |
| 2014/0336493 A1 | 11/2014 | Kulach et al. | |
| 2015/0057634 A1 | 2/2015 | Mastrototaro et al. | |
| 2015/0150457 A1 | 6/2015 | Wu et al. | |
| 2015/0151051 A1 | 6/2015 | Tsoukalis | |
| 2015/0230706 A1 | 8/2015 | Nakagawa et al. | |
| 2015/0231802 A1 | 8/2015 | Quan et al. | |
| 2015/0250639 A1* | 9/2015 | Thirstrup | A61F 13/00051 156/278 |
| 2015/0257923 A1* | 9/2015 | Thirstrup | A61F 13/42 604/318 |
| 2015/0272495 A1 | 10/2015 | Greener | |
| 2015/0328389 A1 | 11/2015 | Heppe | |
| 2015/0342777 A1 | 12/2015 | Seres et al. | |
| 2015/0374896 A1 | 12/2015 | Du et al. | |
| 2016/0008182 A1 | 1/2016 | Prokopuk et al. | |
| 2016/0058604 A1 | 3/2016 | Wiltshire et al. | |
| 2016/0084869 A1 | 3/2016 | Yuen et al. | |
| 2016/0103966 A1 | 4/2016 | Mirza | |
| 2016/0117062 A1 | 4/2016 | Hussam et al. | |
| 2016/0158056 A1* | 6/2016 | Davis | A61F 5/443 29/872 |
| 2016/0158517 A1 | 6/2016 | Nebbia | |
| 2016/0158969 A1 | 6/2016 | McLane et al. | |
| 2016/0166438 A1 | 6/2016 | Rovaniemi | |
| 2016/0178387 A1 | 6/2016 | Yamasaki et al. | |
| 2016/0198996 A1 | 7/2016 | Dullen | |
| 2016/0218555 A1 | 7/2016 | Slaby et al. | |
| 2016/0235581 A1 | 8/2016 | Keleny et al. | |
| 2016/0235582 A1 | 8/2016 | Moavenian | |
| 2016/0242654 A1 | 8/2016 | Quinlan et al. | |
| 2016/0267769 A1 | 9/2016 | Rokhsaz et al. | |
| 2016/0278990 A1 | 9/2016 | Chen | |
| 2016/0305776 A1 | 10/2016 | Mrtensson et al. | |
| 2016/0310077 A1 | 10/2016 | Hunter et al. | |
| 2016/0310140 A1 | 10/2016 | Belson et al. | |
| 2016/0310329 A1 | 10/2016 | Patel et al. | |
| 2016/0331232 A1 | 11/2016 | Love et al. | |
| 2016/0331235 A1 | 11/2016 | Nyberg et al. | |
| 2016/0361015 A1 | 12/2016 | Wang et al. | |
| 2017/0042614 A1 | 2/2017 | Salahieh et al. | |

(56) References Cited

U.S. PATENT DOCUMENTS

| | | |
|---|---|---|
| 2017/0050004 A1 | 2/2017 | Tilson et al. |
| 2017/0055896 A1 | 3/2017 | Al-Ali et al. |
| 2017/0090236 A1 | 3/2017 | Yeh et al. |
| 2017/0098044 A1 | 4/2017 | Lai et al. |
| 2017/0113001 A1 | 4/2017 | Trock |
| 2017/0140103 A1 | 5/2017 | Angelides |
| 2017/0156920 A1 | 6/2017 | Hunt et al. |
| 2017/0181628 A1 | 6/2017 | Burnette et al. |
| 2017/0340474 A1* | 11/2017 | Thirstrup ............... A61B 5/746 |
| 2017/0340498 A1 | 11/2017 | Tessmer et al. |
| 2017/0348137 A1 | 12/2017 | Hvid et al. |
| 2017/0348162 A1 | 12/2017 | Arizti et al. |
| 2017/0360592 A1 | 12/2017 | Carrubba |
| 2017/0360593 A1 | 12/2017 | Cox |
| 2018/0049667 A1 | 2/2018 | Heppe |
| 2018/0055359 A1 | 3/2018 | Shamim et al. |
| 2018/0110078 A1 | 4/2018 | Mandapaka et al. |
| 2018/0136712 A1 | 5/2018 | Niikura et al. |
| 2018/0171183 A1 | 6/2018 | Sakurai et al. |
| 2018/0298240 A1 | 10/2018 | Chatterjee et al. |
| 2018/0318475 A1 | 11/2018 | Thomson et al. |
| 2019/0008439 A1 | 1/2019 | Sageder et al. |
| 2019/0133810 A1 | 5/2019 | Seres et al. |
| 2019/0133811 A1 | 5/2019 | Seres et al. |
| 2019/0133812 A1* | 5/2019 | Seres ............... A61F 5/4404 |
| 2019/0142623 A1 | 5/2019 | Schoess et al. |
| 2019/0175386 A1 | 6/2019 | Monty |
| 2019/0184093 A1 | 6/2019 | Sjolund et al. |
| 2019/0192066 A1 | 6/2019 | Schoess et al. |
| 2019/0192332 A1 | 6/2019 | Hansen et al. |
| 2019/0192333 A1* | 6/2019 | Hansen ............... A61F 5/445 |
| 2019/0192334 A1* | 6/2019 | Hansen ............... A61F 5/445 |
| 2019/0240059 A1 | 8/2019 | Seres et al. |
| 2019/0247050 A1 | 8/2019 | Goldsmith |
| 2019/0252079 A1 | 8/2019 | Constantin et al. |
| 2019/0374163 A1 | 12/2019 | Faarbaek et al. |
| 2020/0000624 A1 | 1/2020 | Gibbons et al. |
| 2020/0078206 A1 | 3/2020 | Chiladakis |
| 2020/0100931 A1 | 4/2020 | Schoess et al. |
| 2020/0114535 A1 | 4/2020 | Wattam et al. |
| 2020/0188161 A1 | 6/2020 | Seres et al. |
| 2020/0246174 A1* | 8/2020 | Hansen ............... A61F 5/443 |
| 2020/0246175 A1* | 8/2020 | Hansen ............... G01M 3/16 |
| 2020/0246176 A1* | 8/2020 | Hansen ............... A61F 5/445 |
| 2020/0246177 A1* | 8/2020 | Hansen ............... A61F 5/445 |
| 2020/0276063 A1 | 9/2020 | Muñoz Herencia |
| 2020/0279368 A1 | 9/2020 | Tada et al. |
| 2020/0297244 A1 | 9/2020 | Brownhill et al. |
| 2020/0306074 A1 | 10/2020 | Speiermann et al. |
| 2020/0322793 A1 | 10/2020 | Yang |
| 2020/0330258 A1* | 10/2020 | Hansen ............... A61F 5/448 |
| 2020/0330260 A1* | 10/2020 | Hansen ............... A61F 5/4404 |
| 2020/0337880 A1* | 10/2020 | Hansen ............... A61F 5/443 |
| 2020/0337881 A1* | 10/2020 | Hansen ............... A61F 5/443 |
| 2020/0337882 A1 | 10/2020 | Hansen et al. |
| 2020/0337883 A1* | 10/2020 | Hansen ............... A61F 5/44 |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0375809 A1 | 12/2020 | Sullivan et al. |
| 2020/0383637 A1 | 12/2020 | Hansen et al. |
| 2020/0383818 A1* | 12/2020 | Hansen ............... A61F 5/44 |
| 2020/0383819 A1* | 12/2020 | Sletten ............... A61F 5/443 |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1* | 1/2021 | Hansen ............... A61F 5/44 |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1* | 3/2021 | Hansen ............... A61F 5/44 |
| 2021/0085512 A1 | 3/2021 | Hansen et al. |
| 2021/0100533 A1 | 4/2021 | Seres et al. |
| 2021/0128364 A1 | 5/2021 | Cole et al. |
| 2021/0145354 A1 | 5/2021 | Hunt et al. |
| 2021/0177642 A1 | 6/2021 | Andersen et al. |
| 2021/0212855 A1 | 7/2021 | Hansen et al. |
| 2021/0228194 A1 | 7/2021 | Mayberg |
| 2021/0338471 A1 | 11/2021 | Nolan et al. |
| 2021/0361464 A1* | 11/2021 | Larsen ............... A61F 5/445 |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1* | 12/2021 | Hansen ............... A61F 5/44 |
| 2021/0369490 A1 | 12/2021 | Hansen et al. |
| 2021/0370217 A1 | 12/2021 | Kirschman |
| 2021/0386368 A1 | 12/2021 | Carlsson et al. |
| 2022/0000652 A1* | 1/2022 | Thirstrup ............... A61F 5/443 |
| 2022/0031227 A1 | 2/2022 | Cho et al. |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0110585 A1 | 4/2022 | Andersen |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |
| 2022/0304844 A1 | 9/2022 | Carlsson et al. |
| 2023/0059470 A1 | 2/2023 | Hansen et al. |
| 2023/0064734 A1 | 3/2023 | Hansen et al. |
| 2023/0105402 A1 | 4/2023 | Hansen et al. |
| 2023/0117727 A1 | 4/2023 | Hansen et al. |
| 2023/0118594 A1 | 4/2023 | Speiermann et al. |
| 2023/0141297 A1 | 5/2023 | Herold et al. |
| 2023/0141719 A1 | 5/2023 | Emborg et al. |
| 2023/0142141 A1 | 5/2023 | Emborg et al. |
| 2023/0145670 A1 | 5/2023 | Seres et al. |
| 2023/0146436 A1 | 5/2023 | Hansen et al. |
| 2023/0147665 A1 | 5/2023 | Hasbeck et al. |
| 2023/0190509 A1 | 6/2023 | Hansen et al. |
| 2023/0210682 A1 | 7/2023 | Hansen et al. |
| 2023/0233147 A1 | 7/2023 | Hansen et al. |
| 2023/0255811 A1 | 8/2023 | Carlsson et al. |
| 2023/0284932 A1 | 9/2023 | Hansen et al. |
| 2023/0293333 A1 | 9/2023 | Hansen et al. |
| 2023/0293335 A1 | 9/2023 | Hansen et al. |
| 2023/0301818 A1 | 9/2023 | Hansen et al. |
| 2023/0310201 A1 | 10/2023 | Hansen et al. |
| 2023/0329893 A1 | 10/2023 | Olsen et al. |
| 2023/0338005 A1 | 10/2023 | Barthe et al. |
| 2023/0372141 A1 | 11/2023 | Larsen et al. |
| 2023/0414397 A1 | 12/2023 | Hansen et al. |
| 2024/0009020 A1 | 1/2024 | Hansen et al. |
| 2024/0041635 A1 | 2/2024 | Hansen et al. |
| 2024/0180740 A1 | 6/2024 | Hansen et al. |
| 2024/0225539 A1 | 7/2024 | Svanegaard et al. |
| 2024/0261130 A1 | 8/2024 | Hansen et al. |

(56) References Cited

U.S. PATENT DOCUMENTS

FOREIGN PATENT DOCUMENTS

| | | |
|---|---|---|
| CA | 3009449 C | 9/2019 |
| CA | 3002372 C | 3/2021 |
| CA | 2947016 C | 2/2023 |
| CN | 103269668 A | 8/2013 |
| CN | 203786580 U | 8/2014 |
| CN | 104902399 A | 9/2015 |
| CN | 104980878 A | 10/2015 |
| CN | 105588856 A | 5/2016 |
| CN | 106062546 A | 10/2016 |
| CN | 206271160 U | 6/2017 |
| CN | 206450708 U | 8/2017 |
| CN | 105615896 B | 5/2019 |
| CN | 105359167 B | 6/2019 |
| DE | 3437950 A1 | 4/1985 |
| DE | 3836590 A1 | 5/1990 |
| DE | 19953062 A1 | 5/2000 |
| DE | 19900611 C1 | 7/2000 |
| DE | 102011014321 A1 | 9/2012 |
| DE | 102011076219 A1 | 11/2012 |
| EP | 0168967 A1 | 1/1986 |
| EP | 0373782 A1 | 6/1990 |
| EP | 0416397 A1 | 3/1991 |
| EP | 0850076 B1 | 4/2005 |
| EP | 1188157 B1 | 12/2005 |
| EP | 2108345 A1 | 10/2009 |
| EP | 2489561 A2 | 8/2012 |
| EP | 2654646 A2 | 10/2013 |
| EP | 2453851 B1 | 10/2014 |
| EP | 3064179 A1 | 9/2016 |
| EP | 3213727 A1 | 9/2017 |
| GB | 2219679 A | 12/1989 |
| GB | 2225951 A | 6/1990 |
| GB | 2343628 A | 5/2000 |
| GB | 2465742 A | 6/2010 |
| GB | 2542093 A | 3/2017 |
| JP | 04-074882 A | 3/1992 |
| JP | 06-152077 A | 5/1994 |
| JP | 09-010184 A | 1/1997 |
| JP | 11-128352 A | 5/1999 |
| JP | 2000-093448 A | 4/2000 |
| JP | 2001-087299 A | 4/2001 |
| JP | 2002-055074 A | 2/2002 |
| JP | 2002-224093 A | 8/2002 |
| JP | 2005-323981 A | 11/2005 |
| JP | 2007-319561 A | 12/2007 |
| JP | 2014-033745 A | 2/2014 |
| JP | 2014-054368 A | 3/2014 |
| JP | 2014-507182 A | 3/2014 |
| JP | 2014151096 A | 8/2014 |
| KR | 10-2012-0003987 A | 1/2012 |
| NL | 1003904 C2 | 3/1998 |
| RU | 2527155 C2 | 8/2014 |
| TW | 201201783 A | 1/2012 |
| WO | 94/15562 A1 | 7/1994 |
| WO | 97/10012 A1 | 3/1997 |
| WO | 99/33037 A1 | 7/1999 |
| WO | 99/36017 A1 | 7/1999 |
| WO | 00/79497 A1 | 12/2000 |
| WO | 01/13830 A1 | 3/2001 |
| WO | 01/50996 A1 | 7/2001 |
| WO | 02/52302 A2 | 7/2002 |
| WO | 02/99765 A1 | 12/2002 |
| WO | 2004084778 A2 | 10/2004 |
| WO | 2005/038693 A1 | 4/2005 |
| WO | 2005/082271 A2 | 9/2005 |
| WO | 2006/008866 A1 | 1/2006 |
| WO | 2006/094513 A2 | 9/2006 |
| WO | 2007/000168 A1 | 1/2007 |
| WO | 2007/059774 A2 | 5/2007 |
| WO | 2007/070266 A1 | 6/2007 |
| WO | 2007098762 A1 | 9/2007 |
| WO | 2007/133555 A2 | 11/2007 |
| WO | 2007128038 A1 | 11/2007 |
| WO | 2008/057884 A2 | 5/2008 |
| WO | 2009/006900 A1 | 1/2009 |
| WO | 2009/052496 A1 | 4/2009 |
| WO | 2009/107011 A1 | 9/2009 |
| WO | 2009/112912 A2 | 9/2009 |
| WO | 2011/003421 A1 | 1/2011 |
| WO | 2011/004165 A1 | 1/2011 |
| WO | 2011003420 A1 | 1/2011 |
| WO | 2011/061540 A1 | 5/2011 |
| WO | 2011/105701 A2 | 9/2011 |
| WO | 2011/123018 A1 | 10/2011 |
| WO | 2011/139499 A1 | 11/2011 |
| WO | 2011/161254 A2 | 12/2011 |
| WO | 2012/068386 A1 | 5/2012 |
| WO | 2012/076022 A2 | 6/2012 |
| WO | 2012/084987 A2 | 6/2012 |
| WO | 2013/013197 A1 | 1/2013 |
| WO | 2013095231 A1 | 6/2013 |
| WO | 2013164517 A1 | 11/2013 |
| WO | 2014/004207 A1 | 1/2014 |
| WO | 2014/086369 A1 | 6/2014 |
| WO | 2014116816 A1 | 7/2014 |
| WO | 2015/007284 A1 | 1/2015 |
| WO | 2015/014774 A1 | 2/2015 |
| WO | 2015/084462 A1 | 6/2015 |
| WO | 2015/094064 A1 | 6/2015 |
| WO | 2015/187366 A1 | 12/2015 |
| WO | 2015186452 A1 | 12/2015 |
| WO | 2016/132738 A1 | 8/2016 |
| WO | 2016124202 A1 | 8/2016 |
| WO | 2016/166731 A1 | 10/2016 |
| WO | 2016162038 A1 | 10/2016 |
| WO | 2016/192738 A1 | 12/2016 |
| WO | 2017/023794 A1 | 2/2017 |
| WO | 2017/062042 A1 | 4/2017 |
| WO | 2017/067558 A1 | 4/2017 |
| WO | 2017/067560 A1 | 4/2017 |
| WO | 2017/074505 A1 | 5/2017 |
| WO | 2017/088153 A1 | 6/2017 |
| WO | 2017108109 A1 | 6/2017 |
| WO | 2017/136696 A1 | 8/2017 |
| WO | 2017/190752 A1 | 11/2017 |
| WO | 2018/028756 A1 | 2/2018 |
| WO | 2019/094635 A1 | 5/2019 |
| WO | 2019/120432 A1 | 6/2019 |
| WO | 2019/161859 A1 | 8/2019 |
| WO | 2019/161860 A1 | 8/2019 |
| WO | 2019/161863 A1 | 8/2019 |
| WO | 2019/174693 A1 | 9/2019 |
| WO | 2019/174695 A1 | 9/2019 |
| WO | 2019/213623 A1 | 11/2019 |
| WO | 2020/035121 A1 | 2/2020 |

\* cited by examiner

SENSOR PATCH FOR AN OSTOMY APPLIANCE

The present disclosure relates to a sensor patch for attachment to a base plate of an ostomy appliance. In particular, the present disclosure relates to the geometrical build of such a sensor patch.

BACKGROUND

Stomal output often contains body fluids and visceral contents that are aggressive to both the skin of a user and to ostomy devices, these have a detrimental effect on the efficiency and integrity of the adhesive materials that are applied to attach the ostomy device to the user's skin surface. For users in general safe, reliable and efficient ostomy devices are evidently highly desirable.

However, a particularly major and persistent concern of a large population of ostomists continues to be failure of the base plate adhesive attaching the ostomy appliance to the user's skin surface, because such failure almost inevitably leads to embarrassing and stigmatizing leakage incidents. Such incidents in turn are known from several user interviews to lead to a reduced quality-of-life feeling. Adhesive failure of the base plate adhesive can result from various reasons. Most often, a leakage incident is caused by stomal output entering between the proximal surface of the base plate and the user's skin, e.g. due to less-than-optimal attachment of the base plate to the skin arising from e.g. uneven skin surface or skin folds. This undesirable progression of stomal output "underneath" the adhesive leads to deterioration and/or weakening of the adhesive material carrying the weight and providing the seal of the ostomy appliance. Often such failure happens surprisingly fast and is only detectable for the user once the failure has already become so severe that leakage occurs, requiring immediate change of the ostomy appliance and possibly also of the user's clothes.

In other instances, the primary factor of adhesive failure is simply a question of how much time has elapsed since the base plate of the ostomy appliance was first applied to the user's skin surface. In addition to the output from the stoma itself, the peristomal skin surface continuously secretes some moisture (e.g. sweat). To mitigate this, most often adhesives of base plates for ostomy devices include hydrocolloid materials which are capable of absorbing high levels of moisture, thereby stabilizing the polymer matrix of the adhesive material and prolonging the lifetime ("wear time") of the base plate. However, eventually the adhesion capability of the base plate no longer can support the force exerted on the base plate from the load of the output collecting bag, and the appliance must be replaced.

As there can be considerable differences in the severity and/or speed by which adhesive failure and potentially leakage occur, which differences at least to some extent are correlated to various factors including those presented above, a mere indication that failure or leakage is imminent, or that it has already occurred, fails to represent a reliable and satisfactory solution to the problem of avoiding sudden embarrassing and stigmatizing leakage incidents in ostomy appliances. In other words, the users of ostomy appliances could greatly benefit from an appliance solution which provides them with better guidance and options regarding how and—not least—how quickly to react to beginning failure or leakage of the adhesive of the base plate of the appliance. More generally, ostomists and health care professionals alike would welcome improvements in ostomy devices to reduce or eliminate the occurrence of sudden leakage incidents.

SUMMARY

The disclosure relates to a sensor patch for an ostomy appliance according to appended claim 1 and the claims dependent thereon.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1A:
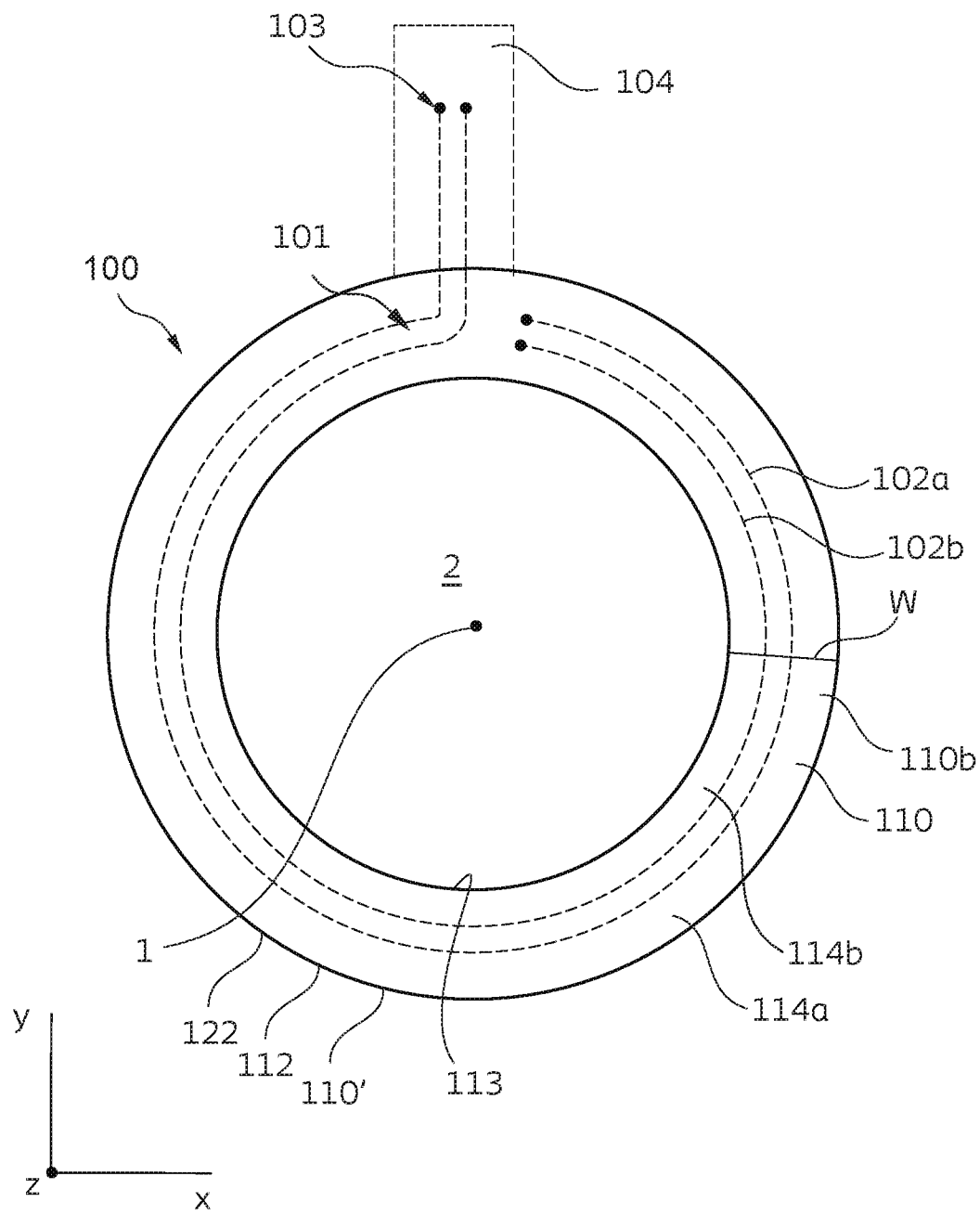
FIG. 1A illustrates a top view of an embodiment of a sensor patch.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a center portion of the ostomy appliance than an element referenced as "inner". In addition, "innermost" should be interpreted as the portion of a component forming a center of the component and/or being adjacent to the center of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to mean at least—for a structural feature: that a majority or major portion of such feature exhibits the characteristic in question, and—for a functional feature or an effect: that a majority of outcomes involving the characteristic provide the effect, but that exceptionally outcomes do no provide the effect.

In a first aspect of the invention, a sensor patch for attachment to a base plate of an ostomy appliance is disclosed. The sensor patch comprises a distal surface, a proximal surface, and an outer contour, the distal surface being adapted for attachment to an adhesive surface of the base plate, and the proximal surface being adapted for attachment to the skin surface of a user. The sensor patch further comprises one or more electrodes comprising a spatial layout, and a planar adhesive layer having a proximal side and a distal side and comprising a first spatial shape. The first spatial shape of the adhesive layer generally corresponds to the spatial layout of the one or more electrodes.

In embodiments, the adhesive layer comprises a proximal surface on the proximal side of the adhesive layer, and a distal surface on the distal side of the adhesive layer. In embodiments, the proximal surface of the adhesive layer is the proximal surface of the sensor patch.

By a sensor patch is meant a patch comprising one or more sensors, such that the sensor patch may provide sensing abilities, in particular towards sensing moisture absorbed in the adhesive of the sensor patch and/or presence of liquid on the proximal surface of the sensor patch. According to the first aspect of the invention, the sensors can be provided through the provision of one or more electrodes. A monitor device can be couplable to the one or more electrodes, whereby the monitor device can monitor changes—by mans of an applied voltage—in certain electrical quantities, e.g. resistance, to determine the state or "health" of the sensor patch in the vicinity of the electrodes, in particular the state or "health" of the adhesive layer of the sensor patch.

In embodiments, the sensor patch is adapted for attachment to an adhesive surface of a generic base plate, i.e. the surface of the base plate intended for attachment to the skin of a user. By a generic base plate is meant any type of commonly available base plates in the field of ostomy appliances. In the following, when referring to a base plate, the referral is to a generic base plate in the field suitable for being attached to a sensor patch according to the invention. In embodiments, the distal surface of the sensor patch is adapted for such attachment to the adhesive surface of a base plate. Commonly, the adhesive surface of a base plate is proximal to the skin of a user. Thus, when in use, the sensor patch is configured to be layered between the skin of a user and the adhesive surface of the base plate. The proximal surface of the sensor patch can be adapted for attachment to the skin surface of a user through the provision of an adhesive layer on the proximal surface, e.g. the proximal surface of the sensor patch may be the proximal surface of the adhesive layer of the sensor patch. Thus, the sensor patch may be considered planar or flat to accommodate such use. In embodiments, the one or more electrodes are provided/arranged on the distal side of the adhesive layer, such as one the distal surface of the adhesive layer.

In embodiments, the sensor patch comprises one or more electrodes, such as a plurality of electrodes, such as two, three, four, five, six, seven or more electrodes. The one or more electrodes can be formed, e.g. printed, on a proximal side of a support layer. The support layer, also denoted a support film, can comprise polymeric (e.g. polyurethane, PTFE, PVDF) and/or ceramic (e.g. alumina, silica) materials. In one or more exemplary sensor patches, the support layer is made of thermoplastic polyurethane (TPU). The support layer material can be made of or comprise one or more of polyester, a thermoplastic elastomer (TPE), polyimide, polyimide, Ethylene-vinyl acetate (EVA), polyurea, and silicones. Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A). The one or more electrodes can be formed, e.g. printed, on a distal side of the support layer. The one or more electrodes are electrically conductive and can comprise one or more of metallic (e.g. silver, copper, gold, titanium, aluminium, stainless steel or other), ceramic (e.g. ITO or other), polymeric (e.g. PEDOT, PANI, PPy or other), and carbonaceous (e.g. carbon black, carbon nanotube, carbon fibre, graphene, graphite, or other) materials. In embodiments, the electrodes can be wire electrodes or one-dimensional electrodes, resembling a string or wire. In embodiments, the electrodes can have a width being considerably smaller than their length. In embodiments, the width of the electrodes can be up to 50 times smaller than the length of the electrodes. In embodiments, the electrodes can be less than 3 mm wide, and more than 100 mm long. In embodiments, the one or more electrodes are printed on a support layer.

In embodiments, the adhesive layer of the sensor patch provides an adhesive suitable for attaching the proximal surface of the sensor patch to the skin surface of a user.

In embodiments, the adhesive layer is made of a first composition. The first composition can comprise one or more polyisobutenes and/or styrene-isoprene-styrene. The first composition can comprise one or more hydrocolloids. The first composition can comprise one or more water soluble or water swellable hydrocolloids. The first composition can be a pressure sensitive adhesive composition suitable for medical purposes comprising a rubbery elastomeric base and one or more water soluble or water swellable hydrocolloids. The first composition can comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer can for example be a styrene-butadiene-styrene block copolymer or a styrene-isoprene-styrene block copolymer. Preferably, one or more styrene-isoprene-styrene (SIS) block type copolymers are employed. The amount of styrene block-copolymer can be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semi-synthetic hydrocolloids and synthetic hydrocolloids. In embodiments, the first composition can comprise 20-60% hydrocolloids. A preferred hydrocolloid is carboxymethyl-cellulose (CMC). The first composition can optionally contain other components, such as fillers, tackifiers, plasticizers, and other additives.

In embodiments, the sensor patch extends in a first geometrical plane and has a thickness extending in a direction being normal to said first geometrical plane. Thus, the sensor patch may be considered generally planar (or flat or two-dimensional) and having a thickness as measured in a direction being normal to the plane spanned by the sensor patch. The adhesive layer is planar and can extend in a second geometrical plane, e.g. in a plane coinciding and/or parallel with the first geometrical plane. A periphery of the adhesive layer can be denoted an edge of the adhesive layer. In embodiments, the periphery of the adhesive layer defines the extent of the adhesive layer. In embodiments, the adhesive layer comprises one or more peripheries. In embodiments, the adhesive layer comprises an inner periphery and an outer periphery. In embodiments, the adhesive layer comprises an inner periphery, an outer periphery and one or more intermediate peripheries. In embodiments, the one or more intermediate peripheries define one or more through-going apertures. In embodiments, the adhesive layer comprises a stomal opening. In embodiments, the inner periphery defines the stomal opening, and the outer periphery defines the radial extent of the sensor patch. The above discussions on possible shapes of the adhesive layer is, according to the first aspect of the invention, defined by the spatial layout of the one or more electrodes. In other words, the shape of the adhesive layer reflects/depends on the shape/layout of the one or more electrodes. The adhesive layer has a thickness extending in a direction being normal to the second geometrical plane. In embodiments, the adhesive layer has a substantially uniform thickness. In embodiments, the adhesive layer has a thickness in the range from 0.1 mm to 1.5 mm, e.g. in the range from 0.2 mm to 1.2 mm.

By the one or more electrodes comprising a spatial layout is meant that the electrode(s) is/are provided in a certain spatial arrangement. In embodiments, the spatial layout is a geometric design of one or more electrodes allowing coverage of two- and/or three-dimensional base plate shapes. In embodiments, the spatial layout is a geometric design of one or more electrodes extending in two and/or three dimensions. Thus, by spatial layout is meant the layout of the electrodes. Thus, when discussing the spatial layout is meant how the one or more electrodes is/are provided spatially on/in the sensor patch in relation to each other and/or in relation to the other components of the sensor patch. The spatial layout is a spatial arrangement of the one or more electrodes in two or three dimensions. In embodiments, where two or more electrodes are provided, the two or more electrodes can extend in different directions and/or have different shapes, and as such, a considerable gap can be formed between electrodes. A gap may be considered considerable if the gap, e.g. seen as the perpendicular distance between a first and a second electrode, is greater than 4 mm, or greater than 8 mm. Contrary to this, two or more electrodes may be considered to extend in immediate vicinity if they are separated by less than 4 mm or less than 8 mm. In embodiments, the two or more electrodes extend in parallel. In embodiments, a first set of electrodes (e.g. two or more electrodes) of the spatial layout extend in immediate vicinity and a second set of electrodes (e.g. two or more electrodes) of the same spatial layout are separated from the first set of electrodes by a considerable gap.

In embodiments, the spatial layout comprises/resembles a ring configured to encircle the stoma of a user. In embodiments, the spatial layout constitutes a ring configured to encircle the stoma of a user. A ring may also be denoted an annulus, i.e. a ring-shaped object bounded by two concentric circles. According to the first aspect of the invention, providing the one or more electrodes in a ring prompts/causes that the spatial shape of the adhesive layer is likewise a ring/annulus—the spatial shape of the adhesive layer reflects the spatial layout (here; a ring/annulus) of the one or more electrodes. A ring-shaped sensor patch facilitates monitoring in a full circle about the stoma. In embodiments, the spatial layout is a ring segment, i.e. a ring not forming a full circle. In embodiments, the spatial layout comprises two or more ring segments. In embodiments, the spatial layout can extend from 0 degrees to, but not including, 360 degrees, thus leaving a slit spanning a finite angle space, i.e. a slit having an angle greater than 0. According to the first aspect of the invention, providing the one or more electrodes in a ring segment prompts/causes that the spatial shape of the adhesive layer is likewise a ring segment. A ring-segment shaped sensor patch facilitates easy adjustment of the sensor patch relative to the base plate, as the formed slit allows for increased manipulation of the sensor patch. In embodiments, the spatial layout comprises a first ring and second ring, the first ring encircling the second ring. In embodiments, the first ring and the second ring are separated by a gap greater than 4 mm, or greater than 8 mm, such as at least 20 mm. Providing a sensor patch having two rings/annuluses allows for monitoring a radial progression of liquid and/or moisture absorption in the interface between the skin surface and the sensor patch, and for monitoring different areas of a base plate, such as a convex/concave base plate.

In embodiments, the spatial layout is substantially a two-dimensional or planar layout. In embodiments, the spatial layout is a strip or a ribbon, thus being quasi-one-dimensional. According to the first aspect of the invention, where the spatial layout of the one or more electrodes is a strip or a ribbon, the adhesive layer of the sensor patch is likewise a strip or a ribbon—the spatial layout of the one or more electrodes defines the spatial shape of the adhesive layer.

In embodiments, the spatial layout is substantially a three-dimensional layout. In embodiments, the specific spatial layout of the one or more electrodes of the sensor patch depends on the coverage desired by a user or the properties of a user's stoma, its shape, or the peristomal area or other physical characteristics or requirements. One object of providing a spatial layout of one or more electrodes of the disclosure is to provide and/or improve sensing abilities in the peristomal skin area.

By the adhesive layer comprising a first spatial shape is meant that the adhesive layer has a certain shape. In embodiments, the shape is substantially two-dimensional/planar. In embodiments, the shape is substantially two-dimensional/planar, but may be considered quasi-one-dimensional, e.g. for a strip or a ribbon. In embodiments, the shape is three-dimensional.

In embodiments, the first spatial shape of the adhesive layer depends on the spatial layout of the one or more electrodes. In embodiments where the spatial layout of the one or more electrodes is quasi-one-dimensional, the first spatial shape of the adhesive layer is correspondingly quasi-one-dimensional. In embodiments where the spatial layout of the one or more electrodes is substantially two-dimensional, the first spatial shape of the adhesive layer is correspondingly substantially two-dimensional. In embodiments where the spatial layout of the one or more electrodes is three-dimensional, the first spatial shape of the adhesive layer is correspondingly three-dimensional. In embodiments, the dimensionality of the spatial shape of the adhesive layer corresponds to the dimensionality of the spatial layout of the one or more electrodes.

By the first spatial shape of the adhesive layer generally corresponding to the spatial layout of the one or more electrodes is meant that the shape of the adhesive layer generally conforms to the layout of the one or more electrodes. In other words, the shape of the adhesive layer is similar to the shape of the spatial layout of the one or more electrodes. In even further other words, the spatial layout of the one or more electrodes defines the spatial shape of the adhesive layer. Thus, the choice of spatial layout of the one or more electrodes affects the spatial shape of the adhesive layer. For example, any change in direction of the extension of the one or more electrodes is mirrored by a corresponding change in direction of the extension of the adhesive layer. Thus, in embodiments, the first spatial shape of the adhesive layer depends on the spatial layout of the one or more electrodes. In embodiments, the adhesive layer supports the one or more electrodes in a region immediately adjacent the electrodes. In embodiments, the adhesive layer supports the one or more electrodes in the immediate vicinity of the electrodes. By generally is meant that the shape of the adhesive layer does not necessarily correspond/adapt to small-scale changes in the extent of the one or more electrodes, e.g. for zigzagging electrodes, where such changes in direction may be on the scale of 0-5 mm. In other words, the first spatial shape of the adhesive layer corresponds to the macro-scale spatial layout of the one or more electrodes. Macro-scale is meant to describe overall changes in direction/extent, e.g. changes allowing the one or more electrodes to form a closed ring encircling an ostomy or any like large-scale shapes, rather than small-scale changes, e.g. zigzagging electrodes.

In embodiments, the adhesive layer covers and/or supports the one or more electrodes only in regions where the electrodes are present. In embodiments, the adhesive layer provides the electrodes with adhesive properties, as well as a support, e.g. a structural support. The spatial layout of the one or more electrodes can depend on multiple factors including the desired need for monitoring the state or "health" of the ostomy appliance—in particular the adhesive properties of the base plate or the adhesive layer of the sensor patch—and on the type of base plate used, e.g. flat/planar, convex, or concave, and/or depending on the three-dimensional shape of the skin in the peristomal area. Thus, by the first spatial shape of the adhesive layer generally corresponding to the spatial layout of the one or more electrodes, the area of the sensor patch adhering to a generic base plate is reduced to the area of the adhesive layer.

By the first spatial shape of the adhesive layer generally corresponding to the spatial layout of the one or more electrodes is provided a versatile sensor patch attachable to a generic base plate, where only the regions of electrodes are provided with an adhesive layer. This provides for a minimalistic sensor patch, such that a large area of the generic base plate is exposed to the skin, while the sensor patch provides sensing means in the vicinity of the one or more electrodes. Thereby, the intrinsic properties of the generic base plate may still be exploited, such as its ability to absorb sweat, its adhesive properties, and its means for attaching an ostomy bag. In other words, the sensor patch provides sensing means in the interface between the skin surface of the user and the generic base plate. In particular, by providing a sensor patch having an adhesive layer corresponding in shape to the spatial layout of the one or more electrodes, only regions of these electrodes are covered by adhesive of the sensor patch. Thereby, the sensor patch does not necessarily cover the entire proximal surface of the generic base plate, but only in the regions of the electrodes, such as regions where monitoring is desired. Thus, the intrinsic properties of the base plate may be conserved and thus exploited during use in regions not covered by the sensor patch. Further, the adhesive layer of the sensor patch facilitates that even in regions of the one or more electrodes, the base plate is securely adhered to the skin surface of the user, and that liquid/moisture may be absorbed.

The sensor patch according to the first aspect of the invention provides for monitoring the adhesive properties of the adhesive layer of the sensor patch, which may change due to moisture absorption or liquid propagating in the interface between the skin surface and the adhesive/the base plate. The condition/state of the sensor patch may also be denoted the health of such a sensor patch. The condition or health is used to describe the degree of erosion the sensor patch, in particular the adhesive of the sensor patch, has experienced. Erosion may originate from moisture absorption, e.g. due to sweat or stomal output. Generally, the condition/health of the base plate/sensor patch may deteriorate over time due to absorption of moisture to a point where leakage of output and/or damage to the skin is highly probable.

To be able to accommodate a large range of different generic base plates, including concave, convex, and planar/flat base plates, embodiments of the invention provide an versatile sensor patch, such that the user with ease can apply the sensor patch according to the first aspect of the invention to any type or variety of generic base plates. In particular, the sensor patch according to the first aspect of the invention reduces the risk of forming creases is its adhesive layer because the adhesive layer is only present where electrodes are present, and as such, the sensor patch does not comprise excess adhesive material, i.e. adhesive material where no electrodes are present. Creases can also be denoted folds or wrinkles. For example, creases occur due to excess material of adhesive layer on an inclined surface.

By providing a sensor patch according to the first aspect of the invention, the risk of forming creases during attachment of the sensor patch to a base plate is reduced. In embodiments, an area of the sensor patch, such as the area of its proximal surface, is reduced to the area defined by the adhesive layer (such as the area of the proximal surface of the adhesive layer), which in turn is defined by the spatial layout of the one or more electrodes. Therefore, the risk of forming creases is significantly reduced—there is no excess adhesive material to form creases. In embodiments, one benefit of the first aspect of the invention is that the area defined by the adhesive layer, such as the area of the proximal surface of the adhesive layer, is reduced by limiting the extent of the adhesive layer to the immediate vicinity of the one or more electrodes. Thus, only a relatively small area of a sensor patch is configured to be applied to the adhesive surface of a generic base plate. Thereby, it is possible to provide any generic base plate with sensing means, without compromising the quality, properties, or changing other characteristics of the generic base plate—both in terms of possibly introducing creases in the adhesive to be applied the user, and in terms of the beneficial properties of the adhesive of the generic base plate. Thus, a relatively large area of the adhesive surface of the generic base plate can remain to be attachable to the skin of a user, and only areas of the sensor patch where electrodes are present are to be applied the generic base plate. Further, by allowing a large range of different spatial layouts of one or more electrodes, embodiments of the invention provide for optimizing the sensing abilities to different desires, needs, or types of base plates. For example, a sensor patch suitable for a convex base plate can be provided with a spatial layout of one or more electrodes such that an inner ring of one or more electrodes can be arranged close to the stoma, and an outer ring can be arranged near a rim portion of the convex base plate. Thereby, the region of the convex base plate being inclined (the portion providing the convex profile) can be free from the sensor patch, i.e. free of the adhesive layer of said sensor patch, as no electrodes are provided here. Since no electrodes are provided in the inclined region of the convex base plate, no adhesive layer is consequently provided here. Thus, the sensor patch comprises a through-going aperture in the region of the inclined portion, which reduces the risk of forming creases in the adhesive layer of the sensor patch.

In embodiments, the provision of a substantially two-dimensional (planar) spatial layout of the one or more electrodes allows for the provision of a substantially planar/flat, and thus compact, sensor patch suitable for being layered between a generic base plate and the skin surface of a user. In addition, by the spatial layout being substantially two-dimensional, a large sensing area can be provided, whereby a large area of the peristomal skin area can be monitored by means of the sensor patch comprising such substantially two-dimensional/planar spatial layout of the one or more electrodes. The corresponding nature between the first spatial shape of the adhesive layer and the spatial layout of the one or more electrodes provides for the shape of the adhesive layer to be likewise two-dimensional. Thereby, the dimensionality of the first spatial shape of the adhesive layer is in accordance with the dimensionality of the spatial layout of the one or more electrodes.

In an embodiment, the adhesive layer comprises an outer periphery defining the outer contour of the sensor patch.

In embodiments, the adhesive layer slightly overlaps the one or more electrodes in a plane being parallel to the geometrical plane spanned by the electrodes. Thereby, an increased structural stability to the electrodes is provided. In embodiments, the adhesive layer is slightly wider than the width of the one or more electrodes provided in a spatial layout, the width being measured across the electrodes, i.e. perpendicular to the general extension of the electrodes. In embodiments, the outer periphery of the adhesive layer may be considered the edge or rim of the adhesive layer. Thus, where the adhesive layer is considered substantially two-dimensional/planar, the adhesive layer can comprise an outer periphery. Thus, in embodiments, this outer periphery defines the outer contour of the sensor patch. In embodiments, the spatial shape of the sensor patch corresponds to the spatial shape of the adhesive layer. In embodiments, the outer contour of the sensor patch is limited by the outer periphery of the adhesive layer. In embodiments, the spatial layout of the one or more electrodes can be a ring/annulus having certain dimensions. In such embodiments, the first spatial shape of the adhesive layer is likewise a ring/annulus having the certain dimensions of the spatial layout. In embodiments, the aperture of the ring can be free of adhesive material, if the spatial layout of the one or more electrodes provides for this (i.e. if no electrodes are provided in this region). In embodiments, the adhesive layer can have an inner periphery defining the aperture of the ring, and an outer periphery defining its maximum spatial extent. Thereby, the outer contour of the sensor patch is defined/limited by the outer periphery of the adhesive layer. In embodiments, the outer periphery of the adhesive layer defines a certain area, which, accordingly, is equal in size to the area defined by the outer contour of the sensor patch.

In an embodiment, the proximal side of the adhesive layer comprises a proximal surface having a first area being smaller than a second area defined by the outer contour of the sensor patch.

In embodiments, the adhesive layer is provided with a first area being smaller than the second area defined by the outer contour of the sensor patch, by providing the spatial layout of the one or more electrodes with a central region without electrodes. In other words, if the spatial layout of the one or more electrodes provides for an aperture in the sensor patch, the adhesive layer likewise comprises such an aperture. Consequently, the area of the proximal surface of the adhesive layer (the first area) is smaller than the area defined by the outer contour of the sensor patch as such (the second area), as the latter includes the area of the aperture, which is not included in the first area. Thereby, a sensor patch having a large coverage, as defined by the second area bound by its outer contour, but a small first area of adhesive layer, is provided. Thereby, when the sensor patch is attached to a generic base plate, the sensor patch leaves a large adhesive area of the generic base plate exposed, thereby reducing the otherwise potentially compromising effects of attaching an object to the adhesive surface of a base plate.

In an embodiment, a minimum distance from at least one electrode of the one or more electrodes to a periphery of the adhesive layer is 4 mm, such as measured in a direction parallel to the first geometrical plane.

By minimum distance is meant the distance measured from any point on an electrode of the one or more electrodes to the nearest point on a periphery of the adhesive layer. By providing a lower limit to the distance of minimum 4 mm, in embodiments, the adhesive layer overlaps the one or more electrodes by at least 8 mm (2×4 mm) in a direction perpendicular to the extension of the electrodes. Thus, the width of the adhesive layer, e.g. the perpendicular distance from one periphery/edge of the adhesive layer to another (e.g., opposite edge), is at least two times 4 mm, provided that a single electrode is provided. In case more than one electrode is provided, the width of the adhesive layer may be larger, due to a separation between such electrodes. The region of the adhesive layer not covered by electrodes, but which is within at least 4 mm from such electrodes, can be considered/denoted a rim zone. Thereby, the adhesive layer is allowed to overlap the one or more electrodes, such that adhesive layer is arranged in the vicinity of the one or more electrodes, but provides a certain amount of structural stability to the sensor patch.

In embodiments, two or more electrodes can extend in parallel and/or in immediate vicinity of each other, such that adhesive layer is continuous/integral between the electrodes. The immediate vicinity can be defined as a separation of less than 4 mm, or less than 5 mm, or less than 7.5 mm, or less than 10 mm. Thus, if more than one electrode is provided in the spatial layout, and the electrodes are in immediate vicinity of each other, the electrodes can be supported by a continuous/integral adhesive layer, i.e. where the adhesive layer is not provided with through-going apertures between the electrodes. In embodiments, a rim zone of at least 4 mm is arranged along the extent of the two or more electrodes and can be arranged between two or more electrodes and/or between a periphery of the adhesive layer and one or more electrodes. In embodiments, the area of the adhesive layer (e.g. the area of the proximal or distal surface of the adhesive layer) is greater than the area of the one or more electrodes.

Thereby, the adhesive layer supports the electrodes and additionally covers the rim zone of said electrodes, the rim zone being at least 4 mm according to the embodiment. Thereby, the adhesive layer provides a structural support to the one or more electrodes. Further, the handling of the adhesive layer, and as such of the sensor patch as such, is eased, as the adhesive layer between the electrodes provides for a stiffer sensor patch. The structural support of the one or more electrodes can be increased by providing a wider adhesive layer, whereas a narrower adhesive layer provides a reduced area covering a generic base plate onto which the sensor patch is adapted to be attached.

In embodiments, a minimum distance between the electrodes can be 0.5 mm, or 1 mm, or 2 mm, or 3 mm, or 4 mm, or 5 mm, or 6 mm, or 7 mm, or 8 mm, or 9 mm, or 10 mm. In embodiments, the minimum distance is the minimum perpendicular distance.

In embodiments, the minimum distance from an electrode of the one or more electrodes to a periphery of the adhesive layer, i.e. the width of the rim zone, can be 0.5 mm, 1 mm, or 2 mm, or 3 mm, or 4 mm, or 5 mm, or 6 mm, or 7 mm, or 8 mm, or 9 mm, or 10 mm. In embodiments, the width of the rim zone is measured in a direction parallel to the first geometrical plane. In embodiments, the width of the rim zone is the perpendicular distance from an outermost electrode of one or more electrodes to a periphery of the adhesive layer.

In an embodiment, a maximum distance from at least one electrodes of the one or more electrodes to a periphery of the adhesive layer is 10 mm, such as measured in a direction parallel to the first geometrical plane.

By a maximum distance is meant the maximally allowed distance from any point on at least one electrode of the one or more electrodes to the nearest point on a periphery of the adhesive layer. In embodiments, the maximum distance is 10 mm. In embodiments, the width of the rim zone (distance from a periphery of the adhesive layer to the nearest electrode) is maximally 10 mm. Thereby, it is ensured that the adhesive layer is only provided in what may be considered an immediate vicinity of the electrodes.

In other embodiments, the maximum distance can be 2 mm, 3 mm, 4 mm, 5 mm, 6 mm, 7 mm, 8 mm, 9 mm, 11 mm, 12 mm, 13 mm, 14 mm, 15 mm, 16 mm, 18 mm, 20 mm, 22 mm, 25 mm, 30 mm, 35 mm, 40 mm, 45 mm, or 50 mm. A short maximum distance provides a structurally pliable adhesive layer, whereas a large maximum distance provides a structurally stiff adhesive layer. In addition, a short maximum distance provides a small area of adhesive layer, whereas a large maximum distance provides a large area of adhesive layer. Thus, in embodiments, the maximum distance depends on the type of base plate onto which the sensor patch is to be attached, or other factors. For example, a convex/concave base plate benefits from a small area of adhesive layer, as such small area reduces the risk of creases. Likewise, a flat/planar base plate may benefit from a large area of adhesive layer. Thereby, the adhesive layer of the sensor patch may be configured to substitute the functionality/properties of the original adhesive of the base plate, whereby the extent and/or number of interfaces between adhesives is reduced.

In embodiments, a single electrode is provided, and the width of the adhesive layer supporting the electrode is maximally 20 mm (a rim zone of 10 mm on each side, i.e. 2×10 mm, here neglecting the width of the electrode as such). In embodiments where two or more electrodes are provided in the spatial layout and the two or more electrodes are separated by more than 20 mm, a through-going aperture is provided in the region separating the two or more electrodes. Thereby, a rim zone of the adhesive layer does not extend far into a region where no electrodes are present. Likewise, the provision of through-going apertures in the area where no electrodes are present provides for an increased flexibility of the adhesive layer, and as such for the sensor patch.

In embodiments, the one or more electrodes are provided in a sensor assembly further comprising a support layer. In embodiments, the one or more electrodes is/are printed onto the support layer. In embodiments, the sensor assembly is configured for attachment to a distal surface of the adhesive layer. In embodiments, the sensor assembly corresponds in shape to the first spatial shape of the adhesive layer. In embodiments, the support layer comprises a proximal surface and a distal surface. In embodiments, the one or more electrodes are provided on the proximal surface of the support layer. Thereby, the one or more electrodes are layered/sandwiched between the adhesive layer and the support layer. Thereby, the one or more electrodes are protected, and adapted to sense absorption of moisture in the adhesive layer. In embodiments, the distal surface of the support layer is adapted for attachment to the adhesive surface of a base plate. Thereby, in embodiments, an additional structural support for the one or more electrodes is provided. The additional support can be particularly beneficial in production and assembly procedures. In embodiments, the support layer comprises a second spatial shape being identical to the first spatial shape of the adhesive layer. Thereby, the support layer can accurately cover the distal side of the adhesive layer. The area of the support layer can be equal in size to the area of the adhesive layer.

In embodiments, the one or more electrodes are provided in a sensor assembly. In embodiments, the distal surface of the adhesive layer is adapted for attachment to a sensor assembly comprising the one or more electrodes. In embodiments, the sensor assembly comprises the support layer, whereby the support layer may be considered a top film protecting the distal surface of the adhesive layer. In embodiments, the sensor patch consists of the adhesive layer, one or more electrodes, and the support layer, the one or more electrodes being sandwiched between the adhesive layer and the support layer.

In an embodiment, the adhesive layer comprises an inner periphery defining a stomal opening.

An inner periphery of the adhesive layer is provided in embodiments wherein the spatial layout of the one or more electrodes provides such shape. In embodiments, the one or more electrodes are arranged substantially circular about a center point. Thereby, due to the first spatial shape of the adhesive layer corresponding to the spatial layout of the one or more electrodes, the adhesive layer is likewise circular about such center point. Due to the adhesive layer being provided only in the vicinity of the one or more electrodes, a through-going central aperture covering the center point is provided. The through-going central aperture can be defined by an inner periphery of the adhesive layer and the through-going central aperture can be considered a stomal opening with a center point for surrounding an ostomy. In an embodiment, the diameter of the stomal opening is at least 40 mm, such as at least 50 mm. Thereby, the sensor patch does not obstruct or influence the intrinsic properties of the generic base plate in the immediate vicinity of the stoma, where the base plate adheres directly to the peristomal skin surface. Other spatial layouts can provide a similar central through-going aperture, e.g. previously discussed spatial layouts.

Thereby is provided a sensor patch comprising one or more electrodes and an adhesive layer capable of encircling/surrounding an ostomy. Thereby, the sensor patch can provide sensor capabilities to the peristomal skin area, i.e. the sensor patch can provide means for sensing the state or health of the adhesive layer and/or of possible leakage occurring in the interface between the sensor patch and the skin surface of a user in the peristomal skin area.

In embodiments, the inner and/or outer peripheries of the adhesive layer extend(s) in parallel to at least one of the one or more electrodes.

In embodiments, the distance from at least one or the one or more electrodes to the inner and/or outer periphery is constant. Thus, the width of at least one rim portion of the adhesive layer is constant. Thereby, at least one periphery of the adhesive layer accurately follows/tracks the extent of at least one of the one or more electrodes. According to previous embodiments, a portion of the periphery of the adhesive layer can vary in distance to the one or more electrodes, within the limits set by the minimum distance and the maximum distance.

In an embodiment, the outer periphery and the inner periphery of the adhesive layer are (substantially) concentric circles.

Due to the corresponding nature between the first spatial shape of the adhesive layer and the spatial layout of the one or more electrodes, the peripheries can be provided if the spatial layout of the one or more electrodes provides for this, i.e. if the one or more electrodes form a ring defining an aperture. However, due to the allowance of the width of the rim zone to vary within previously disclosed limits, the one or more electrodes are allowed to comprise small-scale changes in direction, e.g. zigzagging, without affecting the overall spatial shape of the corresponding adhesive layer, which corresponds to the large-scale variation of the spatial layout. In embodiments, large-scale variation comprises the curvature of the spatial layout.

In embodiments, the outer periphery and the inner periphery of the adhesive layer are concentric circles, whereby a ring or annulus of adhesive layer is provided, whereon the one or more electrodes are provided. A ring shape is useful for encircling a stoma. In embodiments, the inner diameter of the inner periphery is greater than 10 mm, or 20 mm, or 30 mm, or 40 mm, or 50 mm, or 60 mm. In embodiments, the width of the ring, i.e. the perpendicular distance between the inner periphery and the outer periphery, depends on the spatial layout of the one or more electrodes. In embodiments, the width of the ring depends on the number of electrodes and their mutual separation. In embodiments, the width of the ring depends on the number of electrodes, their mutual separation and the width of the rim zone. In an embodiment, the width of the adhesive layer as measured from the inner periphery to the outer periphery is less than 25 mm, such as less than 20 mm. In embodiments, the width of the adhesive layer is less than 30 mm. In embodiments, the width of the adhesive layer is less than 40 mm.

In an embodiment, the adhesive layer comprises two or more through-going openings extending from the proximal side of the adhesive layer to distal side of the adhesive layer. In embodiments, the two or more through-going openings are aligned with at least a portion of each of the one or more electrodes. In embodiments, each of the two or more through-going openings are less than 5 mm in diameter, the diameter being the greatest diameter within the opening.

Thereby, liquid, e.g. output originating from a user's stoma, may propagate through the through-going openings and contact the one or more electrodes, in particular portions of the one or more electrodes. In case liquid propagates through a first through-going opening aligned with a first portion of a first electrode and through a second through-going opening aligned with a second portion of a second electrode, the liquid can cause a short-circuiting event indicating presence of liquid in the interface between the skin of a user and the sensor patch. Presence of liquid in the interface can be indicative of an imminent leakage of output from the user's stoma. Thus, the ability to sense such short-circuiting events provides for a possibility of warning the user through appropriate means.

In an embodiment, the sensor patch comprises two or more electrodes including a first electrode and a second electrode for forming a first sensor.

Thereby, the resistance, or any equivalent quantity, of the adhesive layer can be measured across the first and second electrodes through the adhesive layer. Thus, the provision of a first and a second electrode allows for a current to flow through the supporting, integral adhesive layer, whereby characteristics of the adhesive layer can be assessed. The resistance can be indicative of the health of the sensor patch, and as such, the first and second electrode form a sensor. For example, by means of a monitor device applying a voltage to the electrode, the first electrode can be live, and the second electrode can be grounded. By live is meant that current is being measured between the ground electrode and the live electrode. In embodiments, a potential difference/voltage is applied by means of a monitor device across the live electrode and the ground electrode. In embodiments, resistance is calculated by assessing the current and knowing the potential difference/voltage between the live electrode and the ground electrode. In embodiments, the sensor patch comprises a common ground electrode and two or more electrodes. In embodiments, a sensor is formed between any of the two or more electrodes and the common ground. In embodiments, the potential difference/voltage is applied by means of a monitor device couplable to the two or more electrodes.

In an embodiment, the spatial layout of the one or more electrodes is a ring having an inner diameter of not more than 40 mm.

The inner diameter of the ring of one or more electrodes can be measured from the innermost electrode of the one or more electrodes. Due to the shape of the adhesive layer corresponding to the spatial layout, the adhesive layer likewise comprises an inner periphery having an inner diameter of not more than 40 mm. In embodiments, the presence of a rim zone in the adhesive layer causes the diameter of the inner periphery of the adhesive layer to be less than the inner diameter of the spatial layout provided as a ring. As an example, if the adhesive layer is provided with a rim zone of 4 mm, the diameter of the inner periphery is not more than 32 mm (40 mm−(2×4 mm)).

Thereby is provided a sensor patch particularly adapted to surround a user's stoma and provide sensing means within a close distance from the stoma. In embodiments, the ring has a diameter of less than 50 mm, or less than 45 mm, or less than 35 mm, or less than 30 mm, or less than 25 mm. Thereby, the sensor patch can provide an early warning of deterioration of the adhesive properties of the adhesive layer and/or the presence of liquid in the interface between the skin of the user and the sensor patch. Providing a sensor patch close to a user's stoma can be particularly, but not exclusively, useful if the user wears a convex or concave base plate. In a convex/concave base plate, the innermost region (the region closest to the user's stoma) is typically planar, which provides for an easy attachment of a sensor patch. In embodiments, the innermost rim zone provided in the adhesive layer is adjustable by means of cutting the adhesive to accommodate the shape of the user's stoma.

In an embodiment, the spatial layout of the one or more electrodes can be a ring having an inner diameter of at least 40 mm.

The inner diameter of the ring of one or more electrodes can be measured from the innermost electrode of the one or more electrodes. Due to the shape of the adhesive layer corresponding to the spatial layout, the adhesive layer likewise comprises an inner periphery having an inner diameter of at least 40 mm. In embodiments, the presence of a rim zone in the adhesive layer causes the diameter of the inner periphery of the adhesive layer to be less than the inner diameter of the spatial layout provided as a ring. In embodiments, the adhesive layer is provided with a rim zone of 4 mm, whereby the diameter of the inner periphery is at least 32 mm.

Thereby is provided a sensor patch particularly adapted to cover a rim of a user's base plate. The rim of the base plate can be defined as the parts of the base plate being arranged at diameters greater than 40 mm. In embodiments, the ring has a diameter of at least 45 mm, or at least 50 mm, or at least 55 mm, or at least 60 mm, or at least 65 mm. Thereby, the sensor patch can provide a final warning of deterioration of the adhesive properties of the adhesive layer and/or the presence of liquid in the interface between the skin of the user and the sensor patch. Providing a sensor patch in the rim of a user's base plate, i.e. far from the user's stoma, can be particularly, but not exclusively, useful if the user wears a convex or concave base plate. In a convex/concave base plate, the outermost region is typically planar, which provides for an easy attachment of a sensor patch.

In an embodiment, the spatial layout of the one or more electrodes comprises an outer ring of one or more electrodes and an inner ring of one or more electrodes, the outer ring encircling the inner ring.

In embodiments, the outer ring and the inner ring are connected by a bridge extending from a section of the outer ring to a section of the inner ring. In embodiments, the corresponding nature between the first spatial shape of the adhesive layer and the spatial layout of the one or more electrodes means that the adhesive layer likewise comprises an inner ring and an outer ring, provided the separation between the one or more electrodes of the inner ring and the one or more electrodes of the outer ring is greater than the rim zone of the adhesive layer. In embodiments, the space/region between the inner ring of adhesive layer and the outer ring of adhesive layer is a through-going aperture. Thus, the inner ring may be considered hinged to the outer ring, such that the inner ring is displaceable from the geometrical plane of the outer ring.

Thereby is provided a sensor patch particularly suitable for providing sensing abilities to a concave/convex base plate, where the inner ring is attachable to the part of the base plate closest to the user's stoma, and the outer ring is attachable to the rim of the base plate. Thereby, only the bridge connecting the inner and outer ring is to be attached the inclined portion of the base plate. Thereby, the risk of forming creases is reduced, as adhesive layer is absent in a majority of the inclined region of the base plate onto which the sensor patch is attached. Further, the sensor patch can be useful for planar/flat base plates, as the spatial layout provides for sensors (electrodes) close to the stoma as well as along the rim of (distant the stoma) the base plate, without providing an adhesive layer to be attached the base plate in regions where no electrodes are present.

In an embodiment, the sensor patch further comprises a release liner arranged on the proximal surface of the sensor patch.

The release liner is a protective layer that protects the adhesive layer(s) and/or sensor patch as such during transport and storage and is configured to be peeled off by the user prior to use of the adhesive layer of the sensor patch. The release liner can have a stomal opening, such as a release liner stomal opening, with a center point. The release liner can be attached to the proximal surface of the adhesive layer. In embodiments, the release liner covers the area defined by the outer contour of the sensor patch.

DETAILED DESCRIPTION OF THE DRAWINGS

FIG. 1A illustrates a top view of a sensor patch 100 comprising a first electrode 102a and a second electrode 102b arranged in a spatial layout 101. The electrodes 102a, 102b are provided on a distal side 110b of an adhesive layer 110. The distal side 110b is adapted for attachment to an adhesive surface of a base plate (not shown in FIG. 1A). The spatial layout 101 is shown to resemble a majority of a ring and comprises (and ends/starts in) a monitor interface 103. The monitor interface 103 comprises contact points for establishing an electrical connection between the electrodes 102a, 102b and a monitor device capable of controlling and assessing a current/applying a voltage in/across the electrodes. The monitor interface 103 is provided in a neck portion 104 extending radially away from a center point 1 of the sensor patch 100. The neck portion 104 is configured with a length sufficient to extend beyond the extension of a base plate onto which the sensor patch is to be attached.

The electrodes 102a, 102b combine to form a sensor. For example, by means of a monitor device coupled to the electrodes and applying a voltage, the first electrode 102a may be live, and the second electrode 102b may be grounded, whereby changes in relevant electrical quantities, e.g. resistance, can be monitored. Thereby, the sensor patch 100 comprises sensing abilities. For example, the sensor patch is adapted for attachment to a base plate for monitoring the presence or liquid in an interface between the skin surface of a user and the base plate. In addition, the sensor patch can be adapted for assessing the amount of moisture absorbed in the adhesive layer 110, whereby the state or health of the adhesive of the sensor patch can be assessed. The state or health of the adhesive of the sensor patch may be indicative of erosion and can be used for predicting imminent risk of leakage and/or detachment of the base plate as such.

The sensor patch 110 extends in a first geometrical plane—in the illustrated embodiment of FIG. 1A, in the x-y-plane as illustrated by the coordinate system. The thickness of the sensor patch 100 extends in the z-direction, likewise illustrated in the coordinate system. The sensor patch 110 may be considered to be planar.

The adhesive layer 110 comprises a first spatial shape 110'. The first spatial shape 110' generally corresponds to the spatial layout 101. Thus, due to the spatial layout 101 resembling and taking the form of a ring/annulus, the spatial shape 110' of the adhesive layer 110 likewise resembles and takes the shape of a ring/annulus. In the neck portion 104, the shape 110' of the adhesive layer 110 likewise generally corresponds to the spatial layout 101, as the electrodes 102a,102b terminate here, perpendicular to the ring formed by the same electrodes.

The adhesive layer 110 comprises an outer periphery 112 and an inner periphery 113. The outer periphery 112 of the adhesive layer 110 constitutes the outer contour 122 of the sensor patch 100. In the embodiment of FIG. 1A, the inner periphery 113 and the outer periphery 112 are concentric circles for a majority of the sensor patch 100, except in a section of the outer periphery 112 where the spatial layout 101 forms the monitor interface 103 and thus the neck portion 104 of the sensor patch 100. The inner periphery 113 has a diameter being smaller than the diameter of the outer periphery 112, whereby a width W of the adhesive layer 110 is established. The width W is wider than the width of the spatial layout 101, i.e. the separation between the electrodes 102a, 102b. The parts of the adhesive layer 110 extending radially beyond the spatial layout 101 is denoted a rim zone. An outer rim zone 114a and an inner rim zone 114b is indicated. The rim zones 114a,114b provide a structural stability to the adhesive layer 110 supporting the electrodes 102a,102b. Thus, the width W of the adhesive layer 110 is the sum of the separation between the electrodes 102a,102b and the width of the rim zones 114a,114b. For example, each rim zone 114a,114b can extend at least 0.5 mm away from the electrodes up to a maximum of 10 mm. Thus, the shape 110' of the adhesive layer 110 corresponds to the spatial layout 101 of the electrodes 102a,102b, and comprises rim zones 114a,114b for providing additional structural support and stability.

A central region of the sensor patch 100 is defined by the inner periphery 113. In the embodiment of FIG. 1A, the central region forms a through-going aperture 2 in which adhesive layer 110 is absent. The through-going aperture 2 can constitute a stomal opening for allowing the sensor patch 100 to encircle a stoma. In the central region defined by the inner periphery 113, no material is present. Thereby, the area of the adhesive layer 110 is smaller than the area defined by the outer periphery 112, as the latter includes the area of the through-going aperture 2 in which adhesive layer 110 is absent. Thereby, the sensor patch 100 is configured to cover a substantial portion of a peristomal skin area of a user in use, but simultaneously configured to avoid formation creases when applied to a generic base plate. The reduced tendency to form creases arises from the reduced amount of material (adhesive layer), i.e. in the central region. Thus, the sensor patch 100 facilitates monitoring of erosion of the adhesive layer 110 and potentially detection of output present in the interface between the skin surface and the sensor patch 100. Further, the sensor patch 100 only comprises adhesive in the vicinity of the electrodes 102a,102b, whereby the sensor patch 100 does not necessarily compromise the properties of the base plate it is attached to. Thus, the sensor patch 100 provides a minimalistic build, whereby the risk of forming creases in the adhesive layer 110 is reduced (which may lead to increased risk of output propagating in the interface between the skin surface and the base plate) and whereby a majority of the surface of the generic base plate remains exposed to the skin, such that the properties of the base plate may still be exploited.

Figure 1B:
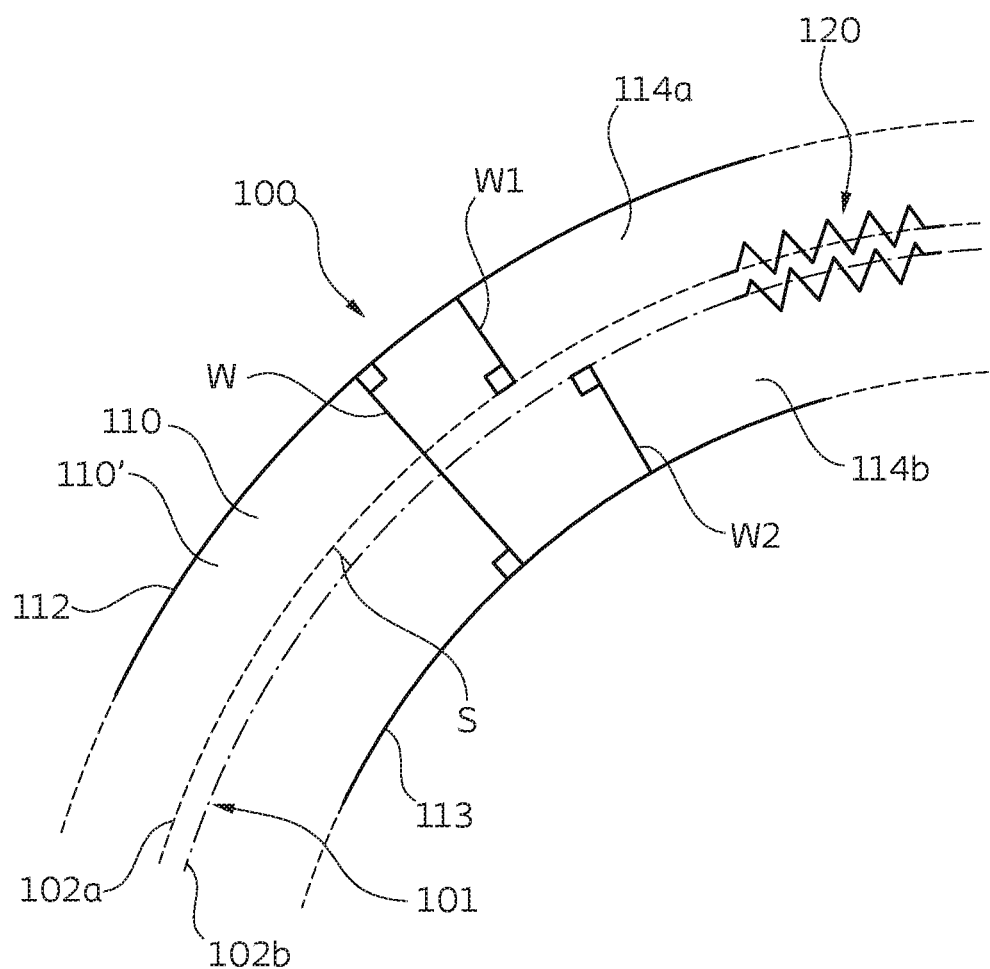
FIG. 1B highlights a section of an embodiment of a sensor patch.

FIG. 1B highlights a section of the sensor patch 100 shown in the embodiment of FIG. 1A. The first 102a and the second electrode 102b comprises a spatial layout 101, i.e. a certain spatial shape in relation to each other. In particular, the spatial layout 101 in FIG. 1B is considered two-dimensional/planar. The first electrode 102a (dashed) and the second electrode 102b (dashed-dotted) extend in parallel to each other and are separated by a gap S. For example, the gap S may be less than 10 mm, such as less than 2 mm. In embodiments, by means of a monitor device coupled to the electrodes and applying a voltage, the first electrode 102a is live, and the second electrode 102b is grounded. The spatial shape 110' of the adhesive layer 110 corresponds to the shape of the spatial layout 101 of the electrodes, as illustrated by the resemblance and/or conformity between the curvature of the spatial layout 101 and the curvature of the outer periphery 112 and the inner periphery 113 of the adhesive layer 110. Thus, the spatial shape 110' of the adhesive layer 110 and the spatial layout 101 has conforming or even identical geometrical characteristics and/or features, including curvature.

A first (outer) rim zone 114a and a second (inner) rim zone 114b of the adhesive layer 110 is illustrated. The rim zones 114a,114b are portions of the adhesive layer 110 extending beyond the electrodes 102a, 102b, such that the width W of the adhesive layer 110 is greater than the separation/gap S between the first 102a and the second electrode 102b. Distances referred to herein are measured in a direction parallel to the first geometrical plane, i.e. in the x-y-plane as illustrated in FIG. 1A. The width W1 of the first rim zone 114a may be defined as the shortest distance between a point on an outermost electrode of the one or more electrodes in the spatial layout 101 (here, the first electrode 102a), and the outer periphery 112. In embodiments, this distance is the perpendicular distance as illustrated. Likewise, the width W2 of the second rim zone 114b can be defined as the shortest distance between a point on an innermost electrode of the one or more electrodes in the spatial layout 101 (here, the second electrode 102b), and the inner periphery 113. Thus, the width W of the adhesive layer 110 is the sum of the width W1 of the first rim zone 114, the width W2 of the second rim zone 114b, and the gap S between the first 102a and the second electrode 102b. In embodiments wherein more electrodes are provided, the first 102a and second electrode 102b may be referred to as the two outermost electrodes of the spatial layout 101. The widths W1, W2 of the rim zones 114a,114b may be equal, such that the adhesive layer 110 is symmetrically arranged about the spatial layout 101 in the first geometrical plane.

In embodiments, the widths W1, W2 of the rim zones 114a,114b are at least 0.5 mm each, in order to provide structural stability to the adhesive layer 110. Further, in embodiments, the widths W1, W2 of the rim zones 114a, 114b are a maximum of 20 mm, or a maximum of 5 mm. Thus, in embodiments the widths W1, W2 are selected between 0.5 mm and 20 mm. In embodiments, the widths W1, W2 are identical, as corresponding to the embodiment illustrated in FIG. 1B. In most cases, the perpendicular distance is the shortest distance, as also illustrated in the embodiments of FIG. 1B. In embodiments, the total width W of the adhesive layer 110 is between 5 mm and 40 mm. In embodiments, the total width W of the adhesive layer 110 is between 15 mm and 30 mm. Providing a total width W of the adhesive layer 110 within the indicated ranges provides a sufficient structural stability, while still reducing the tendency to form creases during use, such as during application to a generic base plate, and while still allowing for exploiting a significant area of the adhesive properties of the generic base plate used.

In the embodiment of FIG. 1B, the inner periphery 113, the outer periphery 112, and the spatial layout 101 are shown to generally extend in parallel. However, small-scale changes in direction of electrodes in the spatial layout 101 do not to affect the overall shape 110' of the adhesive layer 110, as illustrated by the zigzagged electrodes 120. The dashed and dashed-dotted lines illustrating the first and second electrodes (respectively) are illustrated along with the zigzagged lines to illustrate how the curvature of the electrodes are unaffected by the small-scale changes in direction as introduced by the zigzags. Small-scale changes in direction may be changes in direction on distances less than 5 mm (e.g. the wavelength of such zigzags/waves), such as less than 3 mm, occurring in the spatial layout 101. Thus, only large-scale changes in direction of the spatial layout 101 are to be corresponded by or be in conformity with like changes in the spatial shape 110' of the adhesive layer 110. Examples of large-scale changes in direction is the curvature of the electrodes, which is unaffected by the zigzagged electrodes 120, which can be considered small-scale changes.

Figure 1C:
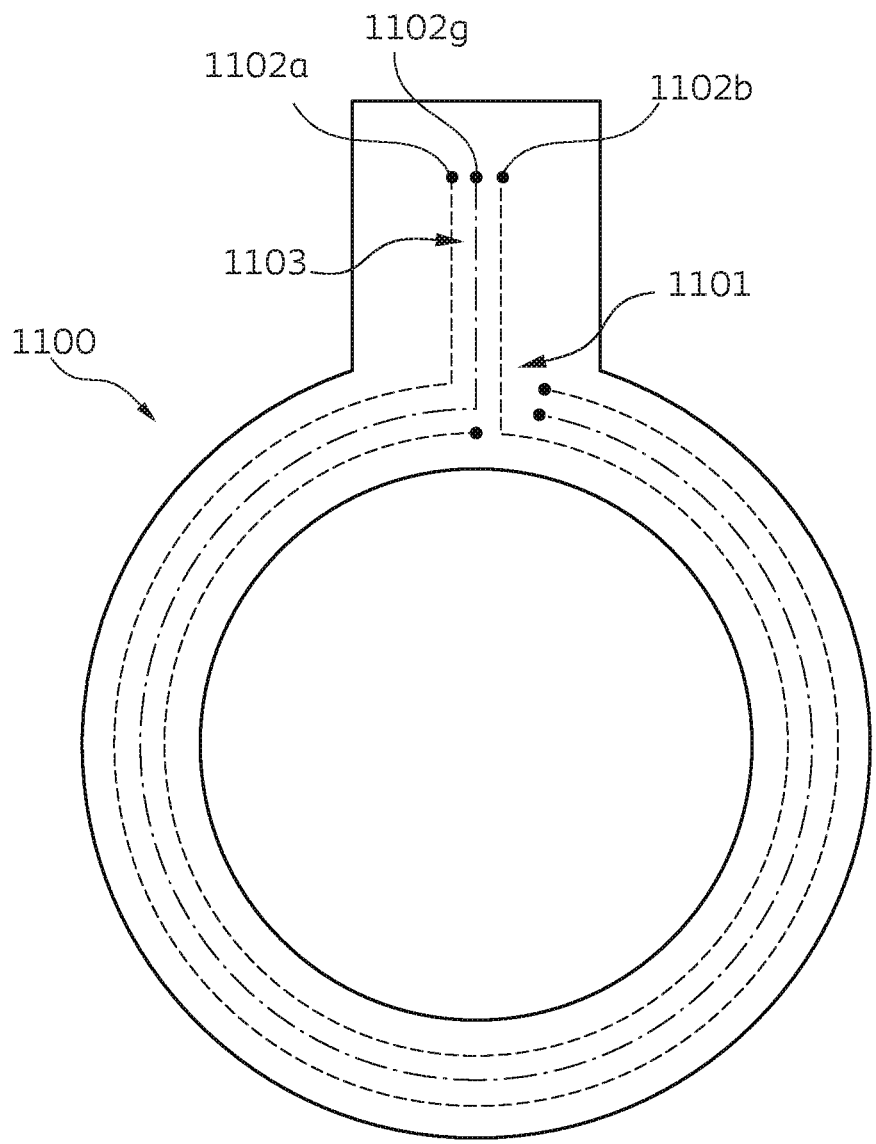
FIG. 1C illustrates a top view of an embodiment of a sensor patch.

FIG. 1C illustrates a sensor patch 1100 having features corresponding to those described in relation to FIG. 1A. However, in FIG. 1C, the spatial layout 1101 comprises three electrodes; a first electrode 1102a, a second electrode 1102b, and a ground electrode 1102g. In embodiments, by means of a monitor device coupled to the electrodes and applying a voltage, the first 1102a and the second electrode 1102b are live. The electrodes 1102a,1102b,1102g comprise connection parts for forming a connection to a monitor device in the monitor interface 1103. The ground electrode 1102g forms the ground for the live first 1102a and second electrodes 1102b. Thereby, two sensors are formed. The first sensor can be formed between the first electrode 1102a and the ground electrode 1102g, and a second sensor can be formed between the second electrode 1102b and the ground electrode 1102g. Again, as was discussed in relation to FIGS. 1A-1B, the spatial shape of the adhesive layer corresponds to the spatial layout 1101 of the electrodes, whereby a ring-shaped sensor patch 1100 is formed in the illustrated embodiment.

Figure 1D:
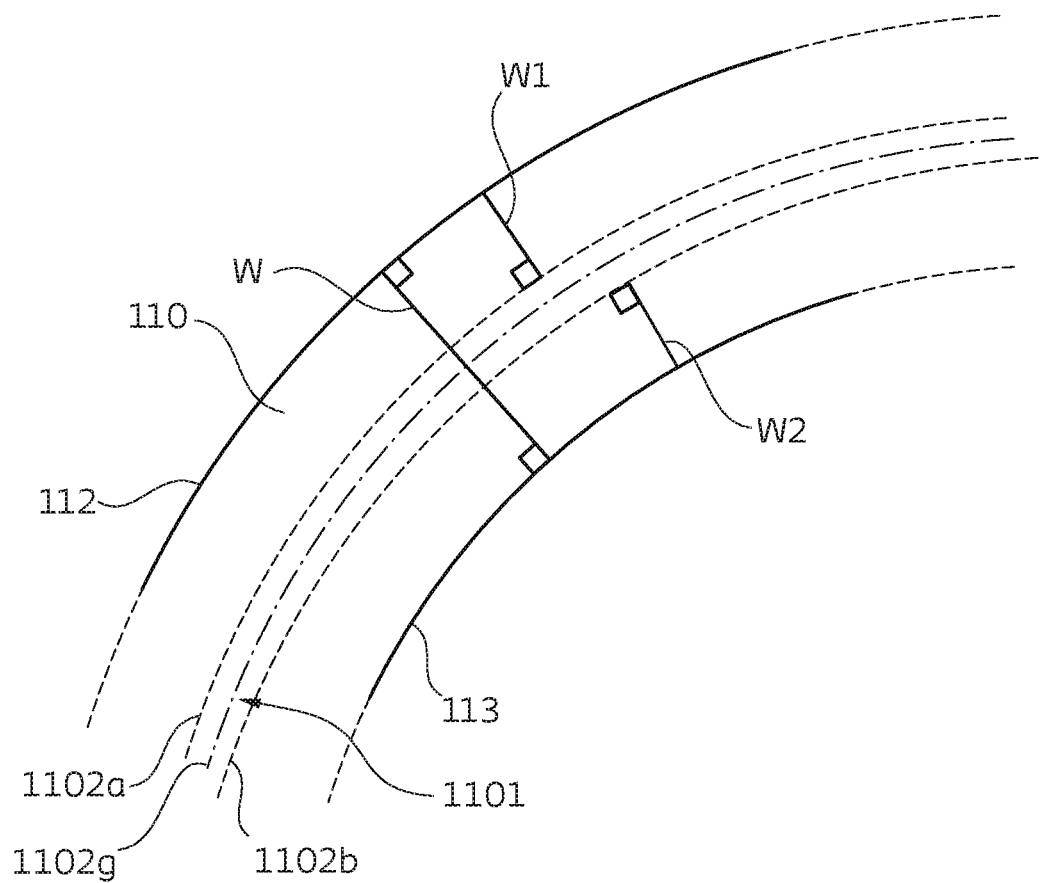
FIG. 1D highlights a section of an embodiment of a sensor patch.

FIG. 1D illustrates the counterpart to FIG. 1B comprising the spatial layout of FIG. 1C. Thus, features of FIG. 1D not referred to hereafter corresponds to features of FIG. 1B. FIG. 1D illustrates how the widths W1,W2 of the rim zones are measured when more than two electrodes are provided in the spatial layout 1101. The first width W1 is measured as the perpendicular distance from an outermost electrode (here, the first electrode 1102a) from the set of electrodes comprising the first electrode 1102a, the ground electrode 1102g, and the second electrode 1102b, to the outer periphery 112 of the adhesive layer 110. Likewise, the second width W2 is measured as the perpendicular distance from an innermost electrode (here, the second electrode 1102b) from the set of electrodes to the inner periphery 113 of the adhesive layer 110. In embodiments, the first width W1 is between 0.5 mm and 20 mm. In embodiments, the second width W2 is between 0.5 mm and 20 mm. In embodiments, the total width W of the adhesive layer 110 is between 10 mm and 40 mm. In embodiments, the total width W of the adhesive layer 110 is between 15 mm and 30 mm.

Figure 2:
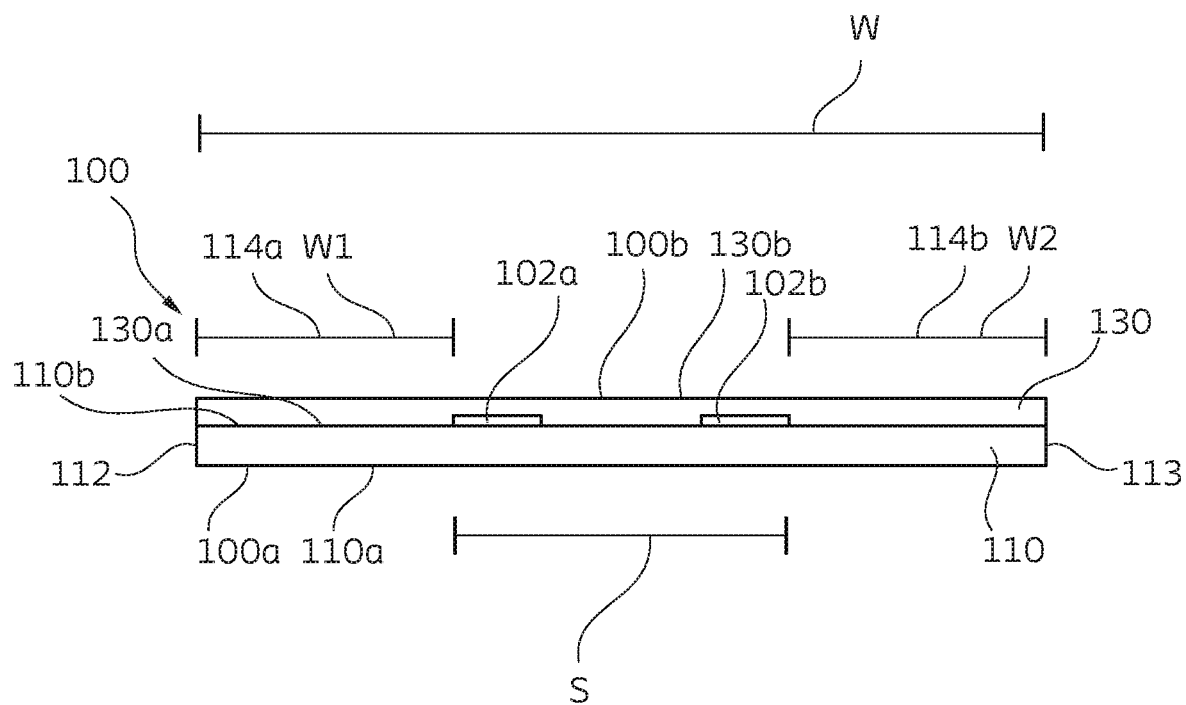
FIG. 2 illustrates a cross-sectional view of an embodiment of a section of a sensor patch.

FIG. 2 illustrates a cross-sectional view of a section of a sensor patch 100. The cross-section may for example be taken across the width W in FIG. 1B.

The sensor patch 100 comprises the adhesive layer 110, two electrodes 102a,102b provided in spatial layout, and a support layer 130. The spatial layout of electrodes is printed onto the support layer 130, such that the support layer 130 supports the electrodes. The adhesive layer 110 comprises a proximal surface 110a and a distal surface 110b. The sensor patch 100 comprises a proximal surface 100a coinciding with the proximal surface 110a of the adhesive layer 110, and a distal surface 100b. The distal surface 100b is coinciding with a distal surface 130b of the support layer 130. The electrodes 102a,102b are sandwiched between the support layer 130 and the adhesive layer 110. The electrodes 102a,102b can be printed onto a proximal surface 130a of the support layer 130. In other words, the electrodes 102a, 102b are sandwiched between a proximal surface 130a of the support layer 130 and the distal surface 110b of the adhesive layer 110. Thereby, the electrodes 102a,102b are adapted to sense moisture absorbed through the adhesive layer 110. Through-going openings (not shown) extending from the proximal surface 110a to the distal surface 110b of the adhesive layer 110 can be provided in the adhesive layer 110. The outer periphery 112 and the inner periphery 113 are highlighted. The support layer 130 covers the entire distal surface 110b of the adhesive layer 110. Thus, in embodiments, the support layer 130 may be considered a top film.

The first rim zone 114a and the second rim zone 114b are illustrated. The first rim zone 114a and second rim zone 114b each extends beyond the electrodes 102a,102b towards the outer periphery 112 and the inner periphery 113, respectively. The first rim zone 114a and the second rim zone 114b has a first width W1 and a second W2, respectively. Thus, the adhesive layer 110 overlaps/extends beyond the spatial layout of the electrodes in the illustrated cross-section. Thus, the overall width W of the adhesive layer is the sum of the widths of the rim zones W1, W2, and the gap S between outer edges of the first 102a and the second electrode 102b. The width of the electrodes is highly exaggerated in the figure, and as such, in embodiments, the width of the electrodes is negligible. The rim zones 114a,114b provide an additional structural stability to the adhesive layer 110. The rim zones 114a,114b terminate by the outer 112 and inner peripheries 113, respectively. Thus, the provision of rim zones 114a,114b does not affect the overall spatial shape of the adhesive layer 110.

Figure 3A:
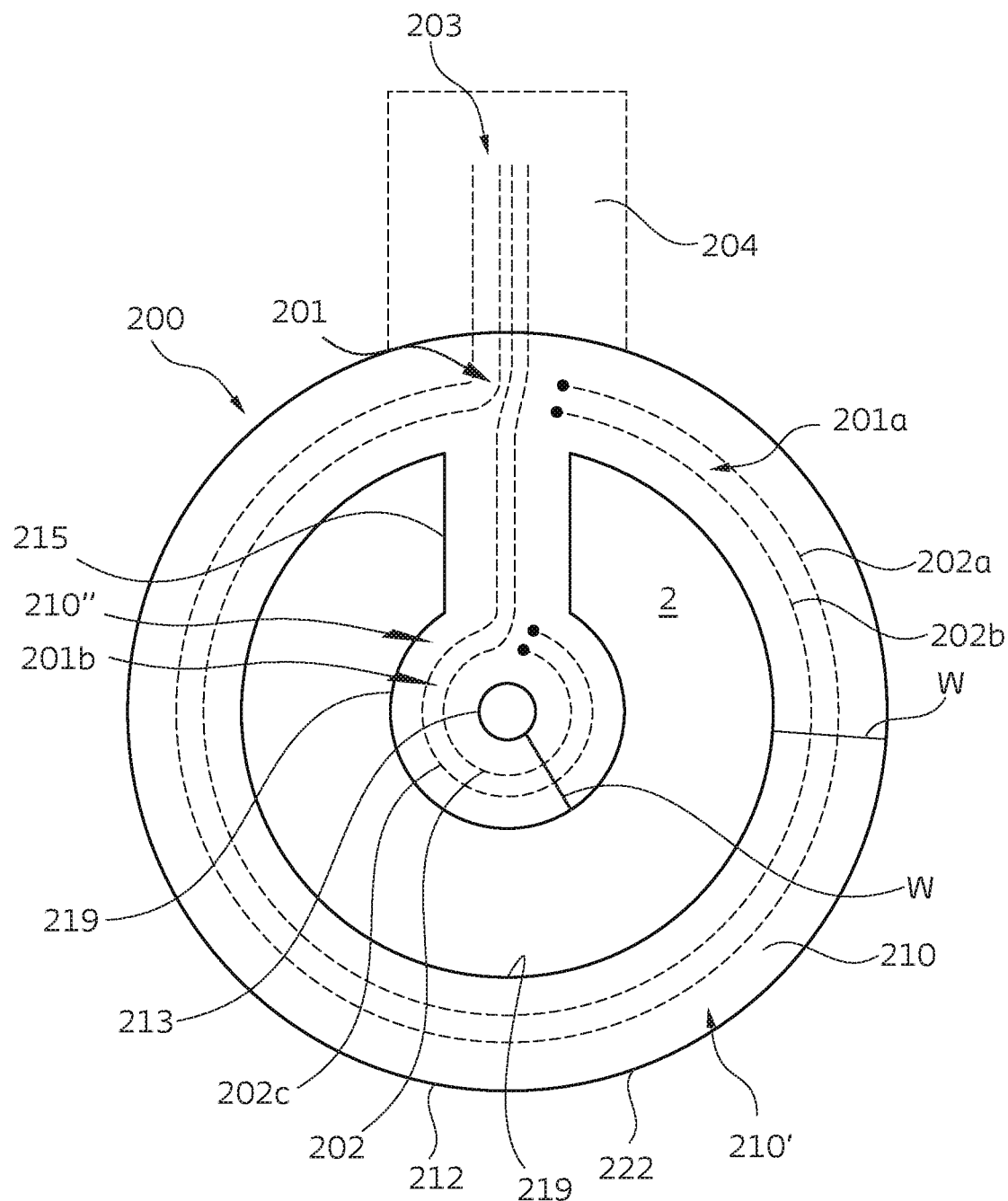
FIG. 3A illustrates a top view of an embodiment of a sensor patch.

FIG. 3A illustrates a top view of an embodiment of a sensor patch 200 according to the invention. The sensor patch 200 comprises four electrodes 202a, 202b, 202c, 202d comprising/arranged in a spatial layout 201. The spatial layout 201 comprises a first (outer) ring 201a comprising the first 202a and the second electrode 202b encircling a second (inner) ring 201b comprising the third 202c and the fourth electrode 202d. The electrodes 202a,202b of the first ring 201a are separated from the electrodes 202c,202d by a distance exceeding the width of the rim zones as discussed in relation to FIG. 1B.

The shape of the adhesive layer 210 generally corresponds/conforms in shape to the spatial layout 201. Thus, the adhesive layer 210 likewise comprises a first (outer) ring 210' corresponding to the outer ring 201a of the spatial layout 201, and a second (inner) ring 210" corresponding to the inner ring 201b. Due to the separation of the electrodes of the first ring 201a from the electrodes of the second ring 201b, a through-going aperture 2 absent of adhesive layer 210 separates the rings, except for a bridge 215 comprising part of the spatial layout 201 connecting the rings. Due to the through-going aperture 2, an intermediate periphery 219 is formed. Thus, the adhesive layer 210 comprises an outer periphery 212 defining the outer contour 222 of the sensor patch 200, an inner periphery 213 defining a stomal opening for receiving a stoma, and an intermediate periphery 219 defining the through-going aperture 2 and the bridge 215. The spatial layout 201 extends into a monitor interface 203, such that the adhesive layer 210 likewise forms a neck portion 204. In embodiments, the width W of the first ring of adhesive layer 210 and the second ring of adhesive layer 210 is identical. In embodiments the width of the rim zones is identical. In embodiments, an upper limit applies to the width of the rim zones, whereby adhesive layer 210 cannot connect the inner ring 210" of adhesive layer 210 and the outer ring 210' of adhesive layer 210. Thus, the spatial shape of the adhesive layer 210 corresponds generally to the spatial layout 201. Only if the spatial layout 201 provides two or more electrodes separated by a distance exceeding two times the selected width of the rim zones, a through-going aperture absent of adhesive layer is to separate the electrodes. The factor of two arises from each of the two electrodes being next to a rim zone, each of said rim zones having a certain width within the limits. For example, a first set comprising one or more electrodes may extend in parallel to each other on a first continuous (unbroken) adhesive layer, while a second set comprising one or more electrodes may extend in parallel on a second continuous adhesive layer. The two adhesive layers can be separated by a through-going aperture when the two sets of electrodes are separated by a distance exceeding two times the selected width of the rim zones. Thereby, the first set of electrodes can form a first sensor capable of assessing the state or health of the first adhesive layer, and the second set of electrodes can form a second sensor capable of assessing the state or health of the second adhesive layer. In embodiments, the first and second adhesive layers are configured to bond through a bridge in certain segments to provide an integral sensor patch, and the adhesive layers may itself be considered integral. Thereby, adhesive layer is only present where the electrodes are present. The provision of rim zones allows two or more electrodes to be provided on an integral piece of adhesive layer, whereby the state or health of the adhesive layer can be assessed. The selected width of the rim zones determines when the adhesive layer is to be separated (e.g. separated by a through-going aperture)—thus, if electrodes are separated by a distance being smaller than such width for the rim zones, the electrodes are arranged on an integral piece of adhesive layer.

As an illustrative example, the width of the rim zones in the sensor patch is set to 4 mm. The specific sensor patch can comprise a first set of electrodes and a second set of electrodes. Two electrodes constituting the first set of electrodes are mutually separated by e.g. 3 mm. Thus, the two electrodes of the first set are provided on an integral adhesive layer. Thereby, the two electrodes of the first set form a sensor capable of assessing an electrical quantity, e.g. resistance, through the adhesive layer. The second set of electrodes likewise comprises two electrodes separated by e.g. 3 mm, and as such are provided on an integral adhesive layer. However, if the separation distance between the first and second set of electrodes exceeds 2×4 mm, i.e. 8 mm, the two sets of electrodes are mutually separated by a through-going aperture/slit. This provides a mutual flexibility between the two sets of electrodes, allowing the two sets of electrodes to be mutually displaced, especially in a z-direction, i.e. in an out-of-plane-direction (cf. FIG. 1A). Further, a reduced amount of adhesive layer in the sensor patch is provided.

Figure 3B:
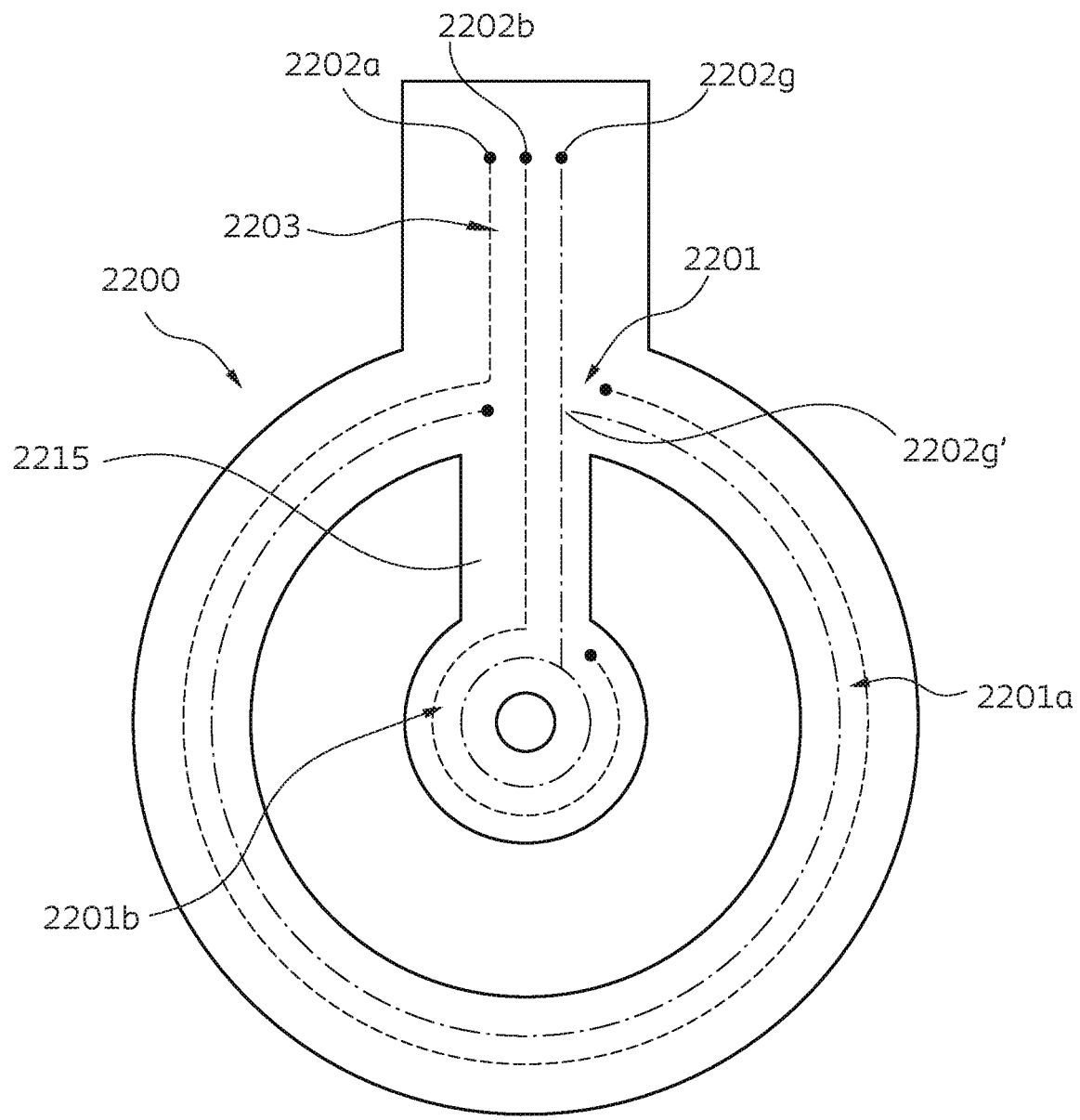
FIG. 3B illustrates a top view of an embodiment of a sensor patch.

FIG. 3B illustrates a sensor patch 2200 having features corresponding to those described in relation to FIG. 3A. However, in FIG. 3B, the spatial layout 2201 comprises three electrodes; a first electrode 2202a, a second electrode 2202b, and a ground electrode 2202g. In embodiments, by means of a monitor device coupled to the electrodes and applying a voltage, the first 2202a and the second electrode 2202b are live. The electrodes 2202a,2202b,2202g comprise connection parts for forming a connection to a monitor device in the monitor interface 2203. The ground electrode 2202g forms the ground for the live first 2202a and second electrodes 2202b. Thereby, two sensors are formed. A first sensor can be formed between the first electrode 2202a and the ground electrode 2202g, and a second sensor can be formed between the second electrode 2202b and the ground electrode 2202g. The ground electrode 2202g extend into both the first (outer) ring 2201a and the second (inner) ring 2201b of the spatial layout 2201. The ground electrode 2202g is split into the first ring 2201a and the second ring 2201b by a split point 2202g' arranged between the bridge 2215 and the monitor interface 2203. Thus, the ground electrode 2202g is a common ground for the first electrode 2202a and the second electrode 2202b.

Figure 4:
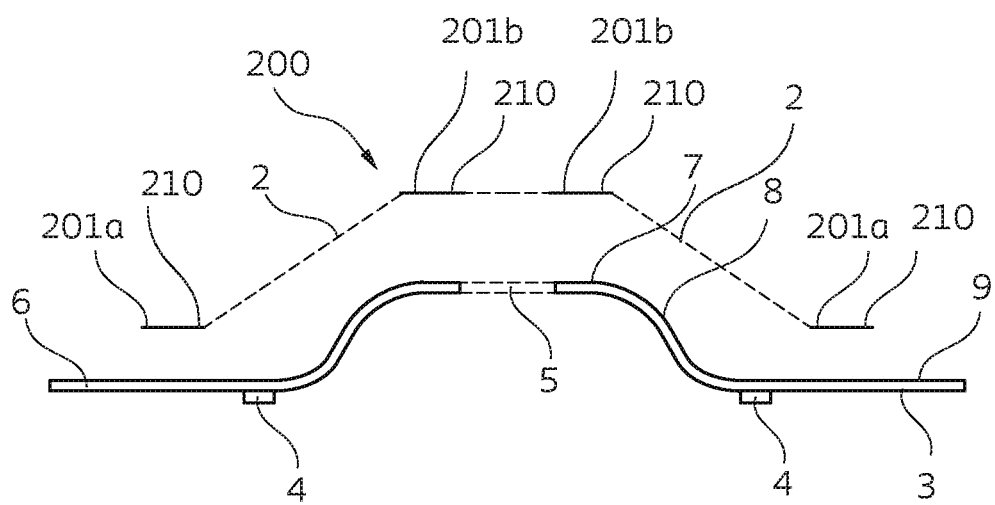
FIG. 4 illustrates a cross-sectional view of a convex base plate and an embodiment of a sensor patch.

FIG. 4 illustrates a cross-sectional schematic view of a convex base plate 3 and the sensor patch 200 of the embodiment of FIG. 3A. The base plate 3 comprises a stomal opening 5 and means 4, such as a first half of a coupling mechanism as otherwise known in the art for attaching an ostomy bag (not shown). The base plate 3 comprises an outer portion 6, an inner portion 7, and an inclined portion 8. The outer portion 6 and inner portion 7 are essentially planar, and extends in two essentially parallel, but mutually displaced geometrical planes. The sensor patch 200 is adapted to be attached to the adhesive surface 9 of the base plate 3, such that the sensor patch 200 is to be sandwiched between the skin surface of a user and the base plate 3. Thus, in regions, the base plate 3 is attached to the skin surface of a user through the generic adhesive surface 9 of the base plate 3, whereas in other regions, the adhesive layer 210 of the sensor patch 200 provides the attachment to the skin surface.

The sensor patch 200 comprises two or more electrodes comprising a spatial layout forming a first (outer) ring 201a and a second (inner) ring 201b. Thus, electrodes are provided in each of the first 201a and second rings 201b. The sensor patch 200 further comprises an adhesive layer 210 corresponding and conforming in shape to the spatial layout. Due to the rings 201a,201b being separated by a distance greater than two times a selected width of the rim zones of the adhesive layer 210, a through-going aperture 2 (i.e., absent of adhesive layer) is formed between the rings 201a,201b. The through-going aperture 2 is indicated with dashed lines. A stomal opening is provided in the central region of the sensor patch 200 and is defined by the inner periphery of the adhesive layer 210 corresponding in shape to the second (inner) ring 201b.

Due to the provision of the through-going aperture 2, the sensor patch 200 can be attached to the convex base plate 3 on the planar regions thereof (i.e., the outer portion 6 and the inner portion 7). Thereby, any risk of forming creases in the sensor patch 200 is reduced or eliminated, as adhesive layer is absent on the inclined portion 8 of the base plate 3. Thus, by applying the described sensor patch 200 to a convex base plate 3, the planar regions are monitored. In other words, the inner portion 7 and the outer portion 6 of the base plate are monitored in terms of the state or health of the adhesive of the sensor patch and/or occurrence of leakage of output, or output propagating in the interface between the skin surface and the sensor patch. The two rings 201a, 201b can be connected by a bridge (not shown).

Figure 5:
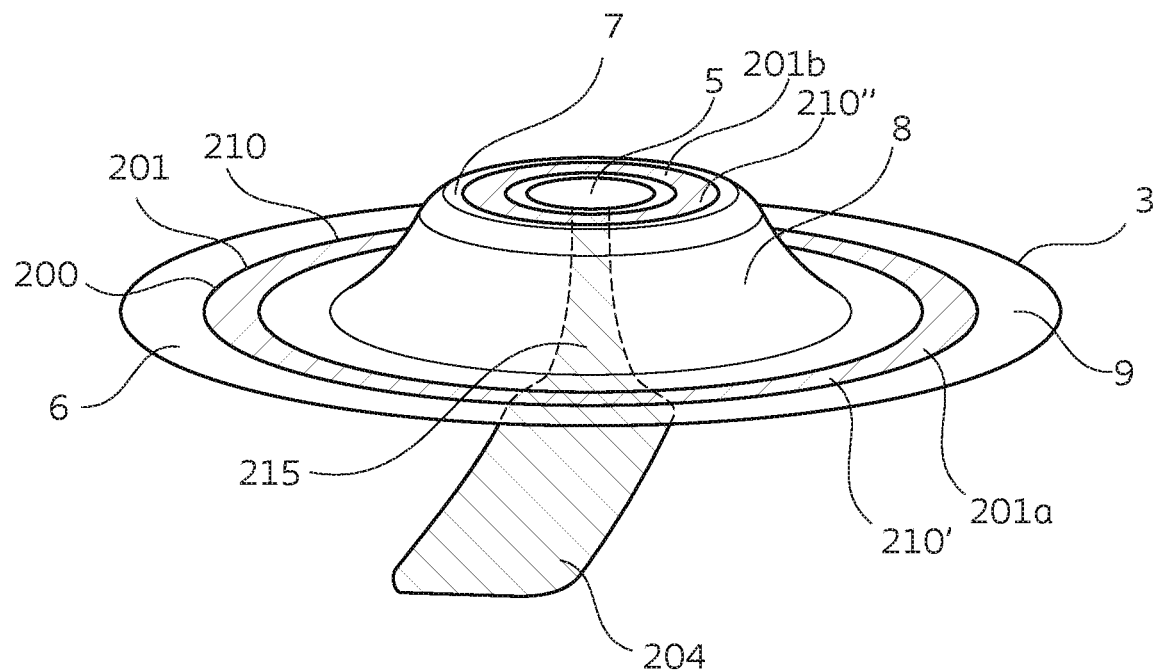
FIG. 5 illustrates a perspective view of a convex base plate having an embodiment of a sensor patch attached.

FIG. 5 illustrates a perspective view of a convex base plate 3 having one embodiment of a sensor patch 200 attached to its adhesive surface 9 (the surface of the base plate adapted for attachment to the skin surface of a user). The sensor patch 200 comprises an adhesive layer 210 corresponding in shape to electrodes comprising a spatial layout 201 provided in the sensor patch 200. Thus, the electrodes form a first (outer) ring 201a encircling a second ring 201b. Due to the corresponding nature of the spatial shape 201 of the adhesive layer 210 and the spatial layout of electrodes, the sensor patch 200 likewise comprises a first ring 210' of adhesive layer encircling a second ring 210'' of adhesive layer. The second ring 210'' of adhesive layer is adapted for attachment to the adhesive surface of an inner portion 7 of the convex base plate 3, whereas the first ring 210' of the adhesive layer is adapted for attachment to the adhesive surface on an outer portion 6 of the convex base plate 3. Due to the absence of adhesive layer adjacent to the inclined portion 8, the sensor patch 200 is less prone to forming creases during attachment to the adhesive surface 9 of the base plate 3.

The first ring 210' and the second ring 210'' are connected through a bridge 215 comprising adhesive layer 210 and a portion of the spatial layout of the electrodes 201. The bridge 215 is sufficiently narrow to reduce the tendency to form creases on the inclined portion 8 of the base plate 3. A neck portion 204 comprises a monitor interface (not shown). The spatial layout 201 provides for such bridge 215 and monitor interface. The neck portion 204 extends beyond the extension of the base plate 3, such that a monitor device may be attached without compromising the adhesion (properties) of the base plate 3 to the skin surface.

Figure 6A:
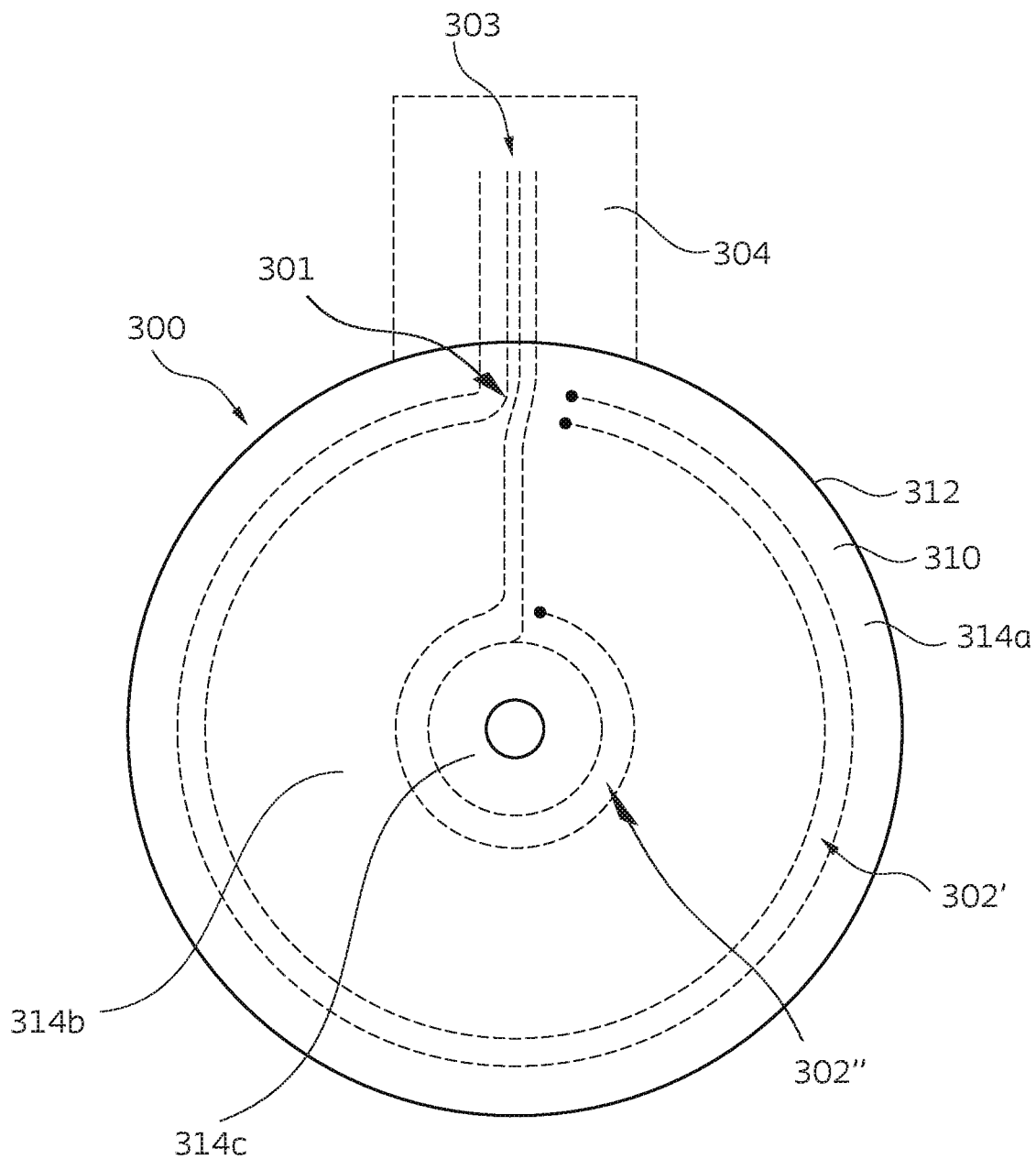
FIG. 6A illustrates a top view of an embodiment of a sensor patch.

FIG. 6A illustrates a top view of an embodiment of a sensor patch 300 having two sets of electrodes 302',302'' comprising a spatial layout 301 and an adhesive layer 310. The rim zones 314a, 314b, 314c vary in width. Thus, the first and third rim zones 314a,314c are narrower than the second rim zone 314b. Thereby, no through-going aperture is provided in the adhesive layer between the two sets of electrodes 302',302''. The third rim zone 314c is illustrated to be identical in width to the first rim zone 314a. Despite varying rim zones, the adhesive layer 310 generally corresponds and conforms to the spatial layout 301, as each of the sets of electrodes and the adhesive layer are generally circular. A monitor interface 303 and a neck portion 304 is provided on a segment of the outer periphery 312 of the adhesive layer 310.

Figure 6B:
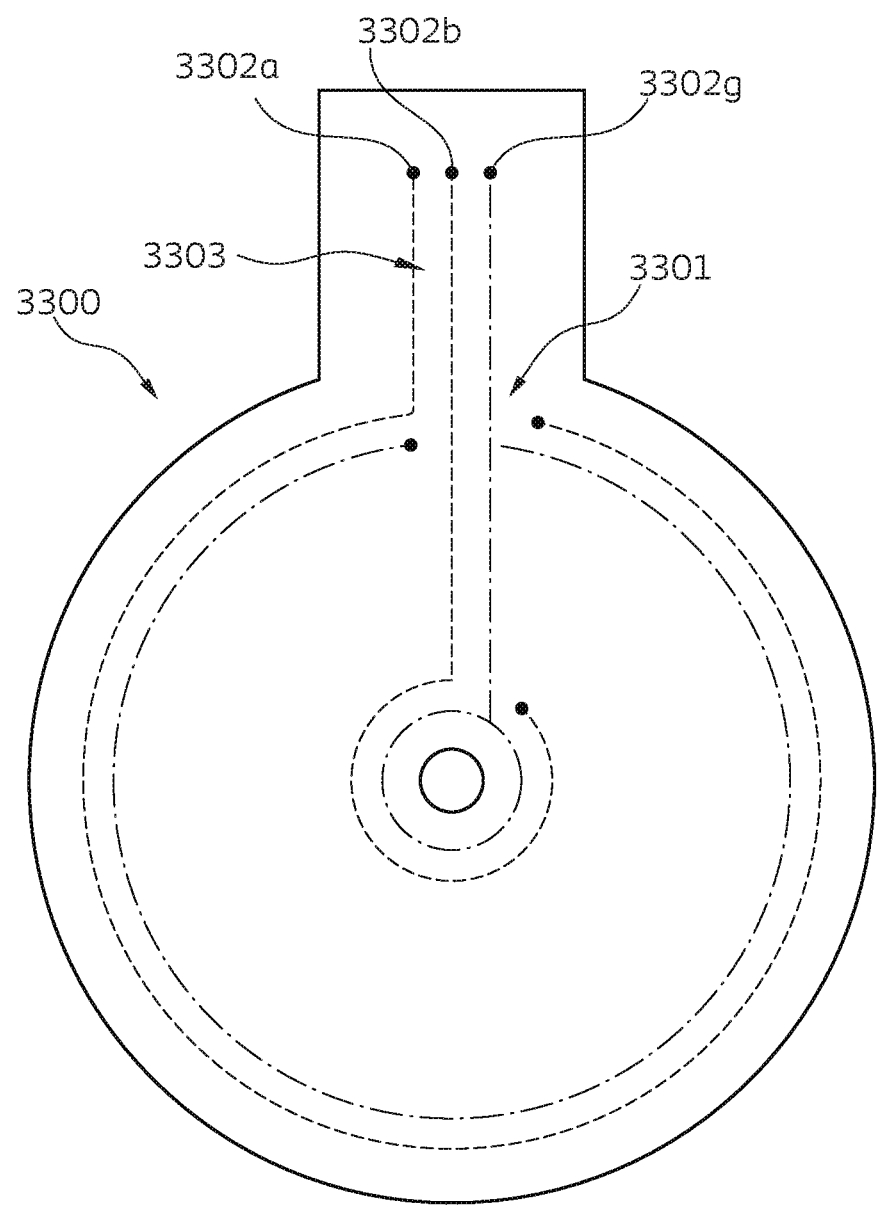
FIG. 6B illustrates a top view of an embodiment of a sensor patch.

FIG. 6B illustrates a sensor patch 3300 having features corresponding to those described in relation to FIG. 6A. However, in FIG. 6B, the spatial layout 3301 comprises three electrodes; a first electrode 3302a, a second electrode 3302b, and a ground electrode 3302g. In embodiments, by means of a monitor device coupled to the electrodes and applying a voltage, the first 3302a and the second electrode 3302b are live. The electrodes 3302a,3302b,3302g comprise connection parts for forming a connection to a monitor device in the monitor interface 3303. The ground electrode 3302g forms the ground for the live first 3302a and second electrodes 3302b. Thereby, two sensors are formed. A first sensor can be formed between the first electrode 3302a and the ground electrode 3302g, and a second sensor can be formed between the second electrode 3302b and the ground electrode 3302g. Thus, the ground electrode 3202g is a common ground for the first electrode 3202a and the second electrode 3202b.

Figure 7:
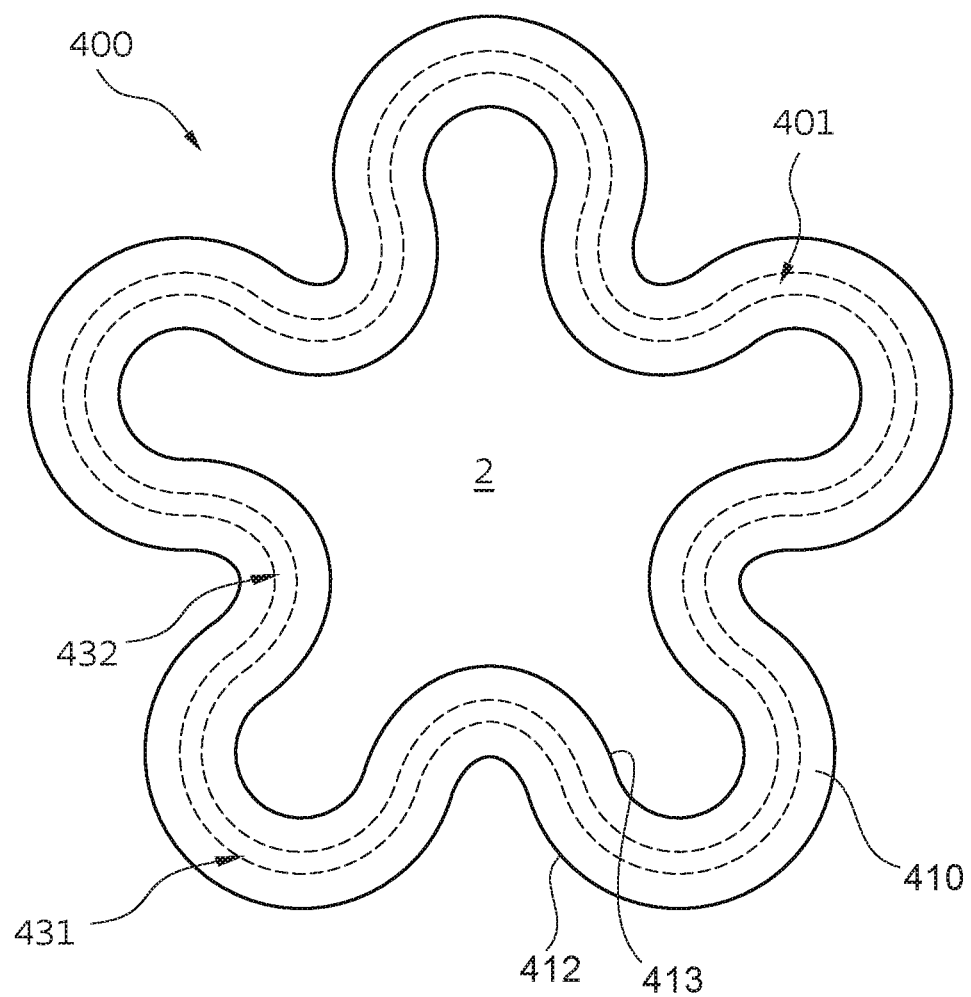
FIG. 7 illustrates a top view of an embodiment of a sensor patch.

FIG. 7 illustrates a top view of a sensor patch 400 having two electrodes comprising a spatial layout 401, and an adhesive layer 410. The spatial layout comprises radially extending tongues 431 with concave portions 432 in between, the tongues and concave portions extending in the geometric plane of the sensor patch. The shape of the spatial layout may be considered flower-shaped or petal-shaped. Due to the corresponding nature between the spatial layout 401 and the spatial shape of the adhesive layer 410, the shape of the adhesive layer 410 comprises like, radially extending tongues with concave portions in between. The outer periphery 412 and the inner periphery 413 of the adhesive layer 410 extend in parallel and are equidistant. The inner periphery 413 defines a through-going aperture 2 absent of adhesive layer. The through-going aperture 2 may be considered a stomal opening for receiving a stoma. The provision of a flower-shaped sensor patch 400 provides for the ability to monitor both inner, intermediate, and outer portions of a base plate onto which the sensor patch 400 is attached, without introducing a large area of adhesive layer 410 increasing the risk of forming creases during attachment. A neck portion (not shown) comprising a monitor interface can be arranged along any segment of the outer periphery.

Figure 8:
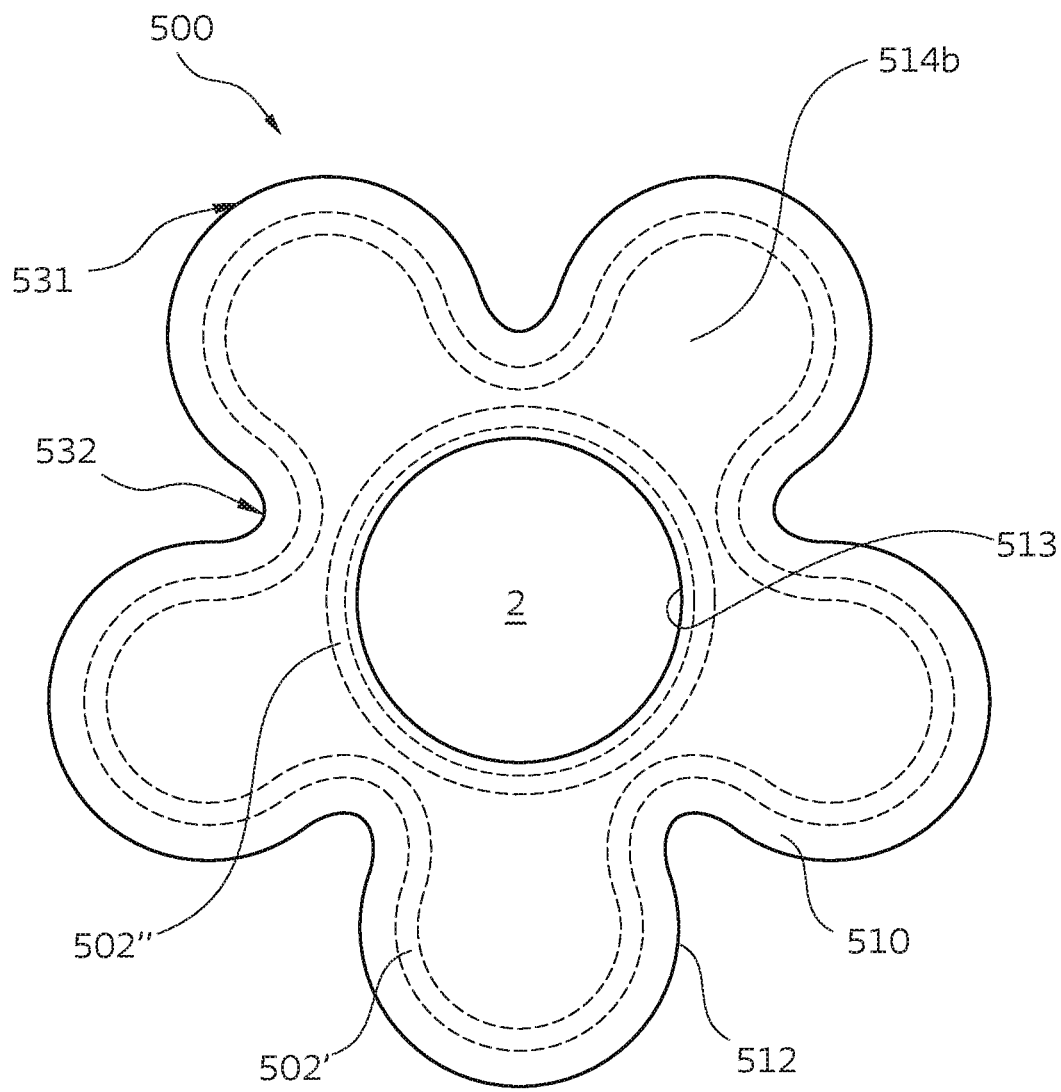
FIG. 8 illustrates a top view of an embodiment of a sensor patch.

FIG. 8 illustrates a top view of an embodiment of a sensor patch 500 having a first set 502' and a second set 502'' of electrodes comprising a spatial layout. The first set of electrodes 502' comprises radially extending tongues 531 with concave portions 532 in between, the tongues and concave portions extending in the geometric plane of the sensor patch. The second set of electrodes 502'' is circular. The first set of electrodes 502' encircles the second set of electrodes 502''. The outer periphery 512 of the adhesive layer 510 extends in parallel to the first set of electrodes

502'. The inner periphery 513 of the adhesive layer 510 extends in parallel to the second set of electrodes 502". An intermediate rim zone 514b arranged between the first set of electrodes 502' and the second set of electrodes 502" varies in width, thus keeping adhesive layer 410 present between the sets of electrodes. The inner periphery 513 defines a through-going aperture 2. The provision of a sensor patch 500 allows for increased/improved monitoring of an inner portion of a base plate (as provided by the second set of electrodes 502" and parts of the first set of electrodes 502'), i.e. in the vicinity of the stoma, while having monitoring capabilities in certain areas of the outer portion of the base plate (as provided by parts of the first set of electrodes 502'). The sensor patch 500 reduces the tendency to form creases when applied a convex/concave base plate due to the provision of tongues. A neck portion (not shown) comprising a monitor interface may be arranged along any segment of the outer periphery.

Figure 9:
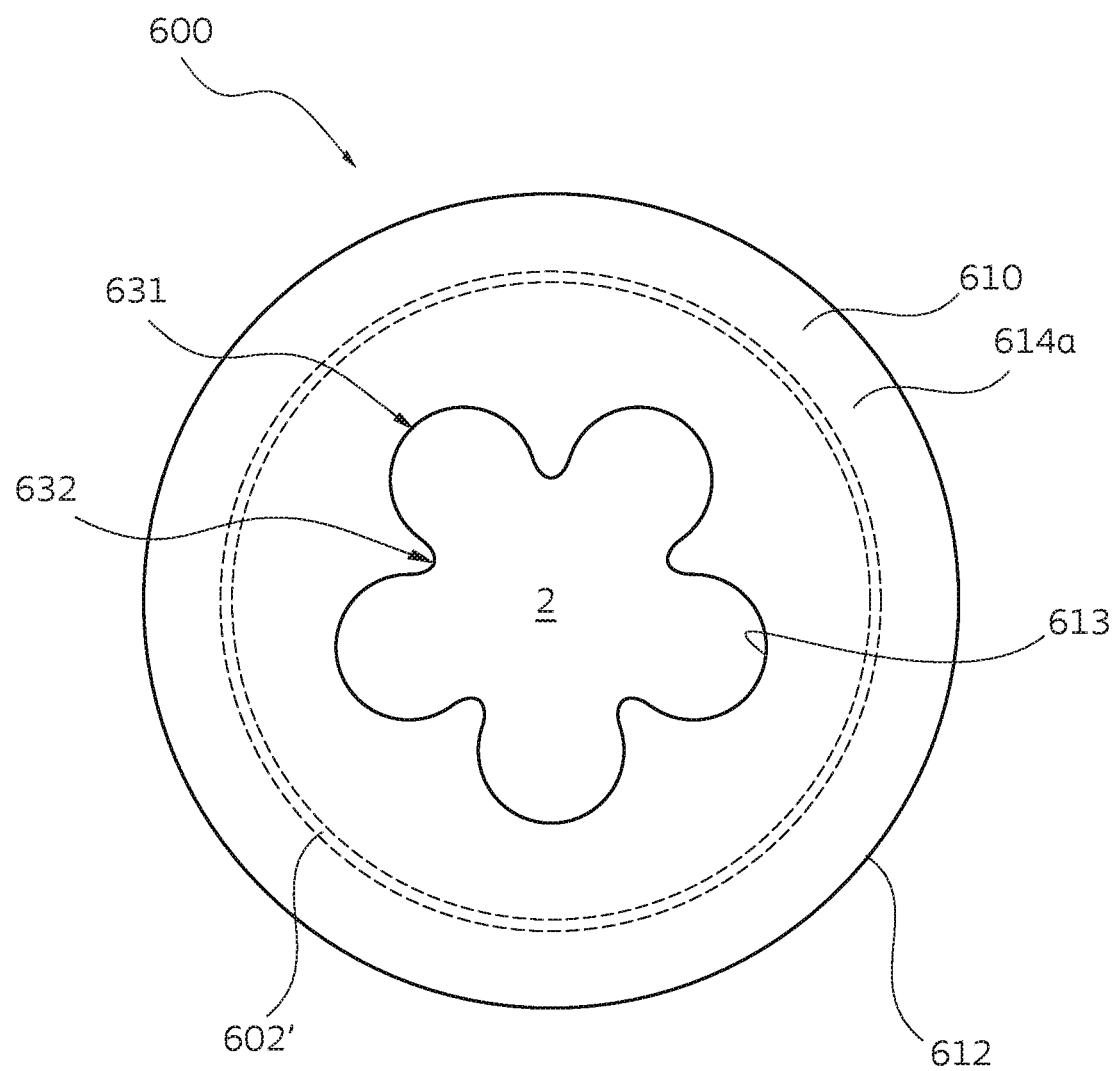
FIG. 9 illustrates a top view of an embodiment of a sensor patch.

FIG. 9 illustrates a top view of an embodiment of a sensor patch 600 having a first set of electrodes 602' comprising a spatial layout. The outer periphery 612 of the adhesive layer 610 is circular and is shown to extend in parallel with the first set of electrodes 602'. The inner periphery 613 of the adhesive layer comprises radially extending tongues 631 with concave portions 632 in between, the tongues and concave portions extending in the geometric plane of the sensor patch. The inner periphery 613 defines a through-going aperture 2 absent of adhesive layer. The inner rim zone 614b varies in width, whereas the outer rim zone 614a is constant in width. The provision of a sensor patch 600 according to the embodiment allows for increased/improved monitoring of an outer portion of a base plate, i.e. distant the stoma, while having an inner periphery 613 reducing the tendency to form creases when applied a convex/concave base plate. A neck portion (not shown) comprising a monitor interface may be arranged along any segment of the outer periphery.

Figure 10:
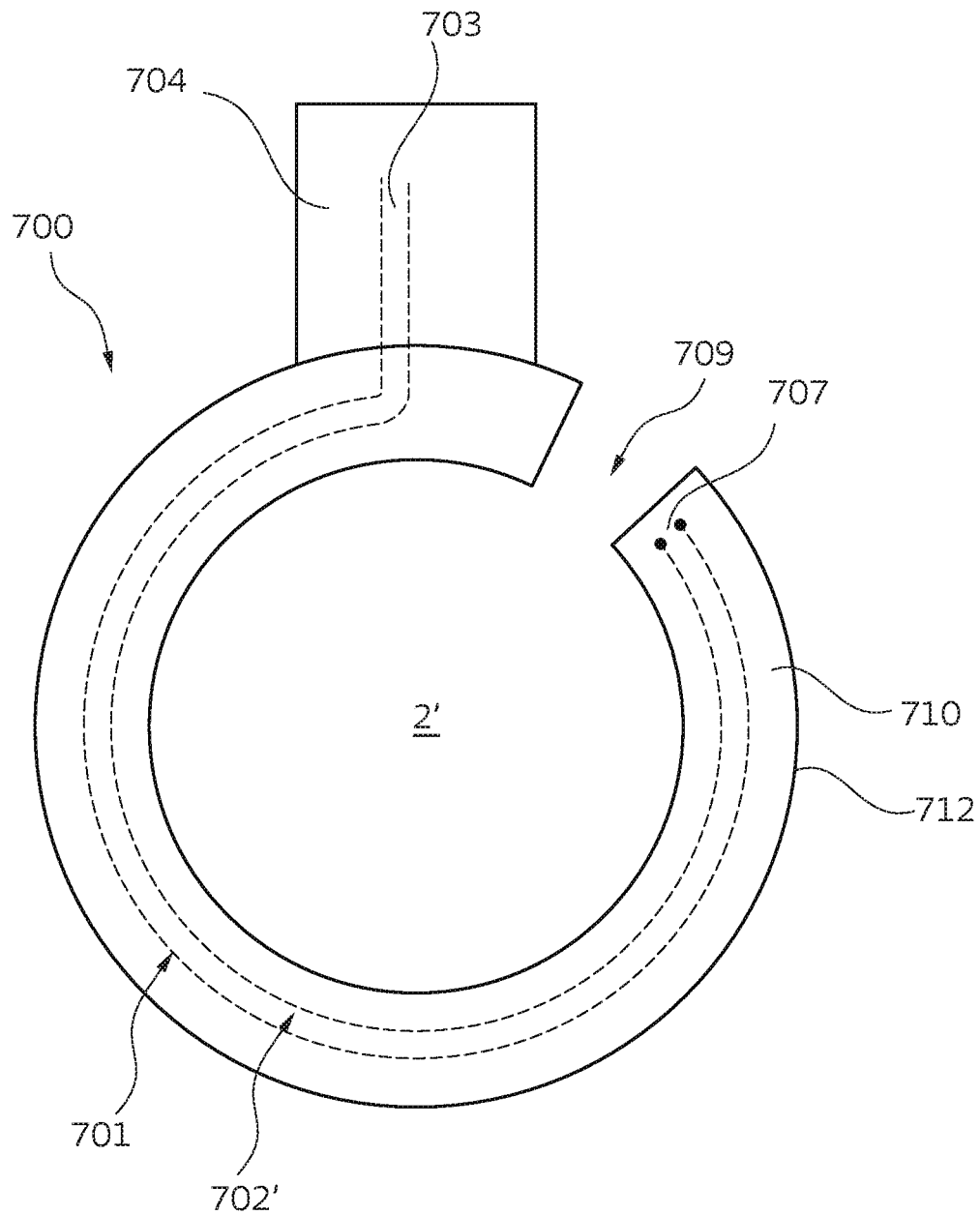
FIG. 10 illustrates a top view of an embodiment of a sensor patch.

FIG. 10 illustrates a top view of a sensor patch 700 having a first set of electrodes 702' comprising a spatial layout 701. The spatial layout 701 is shaped as a portion of a ring, i.e. extending less than 360 degrees. Thus, a slit 709 is formed where the electrodes 702' terminate in a first end 707. The adhesive layer 710 corresponds in shape to the spatial layout 701, including a rim zone on each side of the spatial layout 701, and including where the electrodes 702' terminate in the first end 707 by the slit 709. The slit 709 creates a passage from the surroundings into a partly-encapsulated through-going aperture 2'. The outer contour of the sensor patch 700 may in this embodiment be considered the contour as formed as if no slit were present. A monitor interface 703 and a neck portion 704 is provided on a segment of the outer periphery 712 of the adhesive layer 710. The provision of a slit 709 in the sensor patch 700 eases the attachment procedure, as the flexibility of the adhesive layer 710 allows is to be manipulated/displaced, e.g. around the protruding part of a convex base plate.

Figure 11:
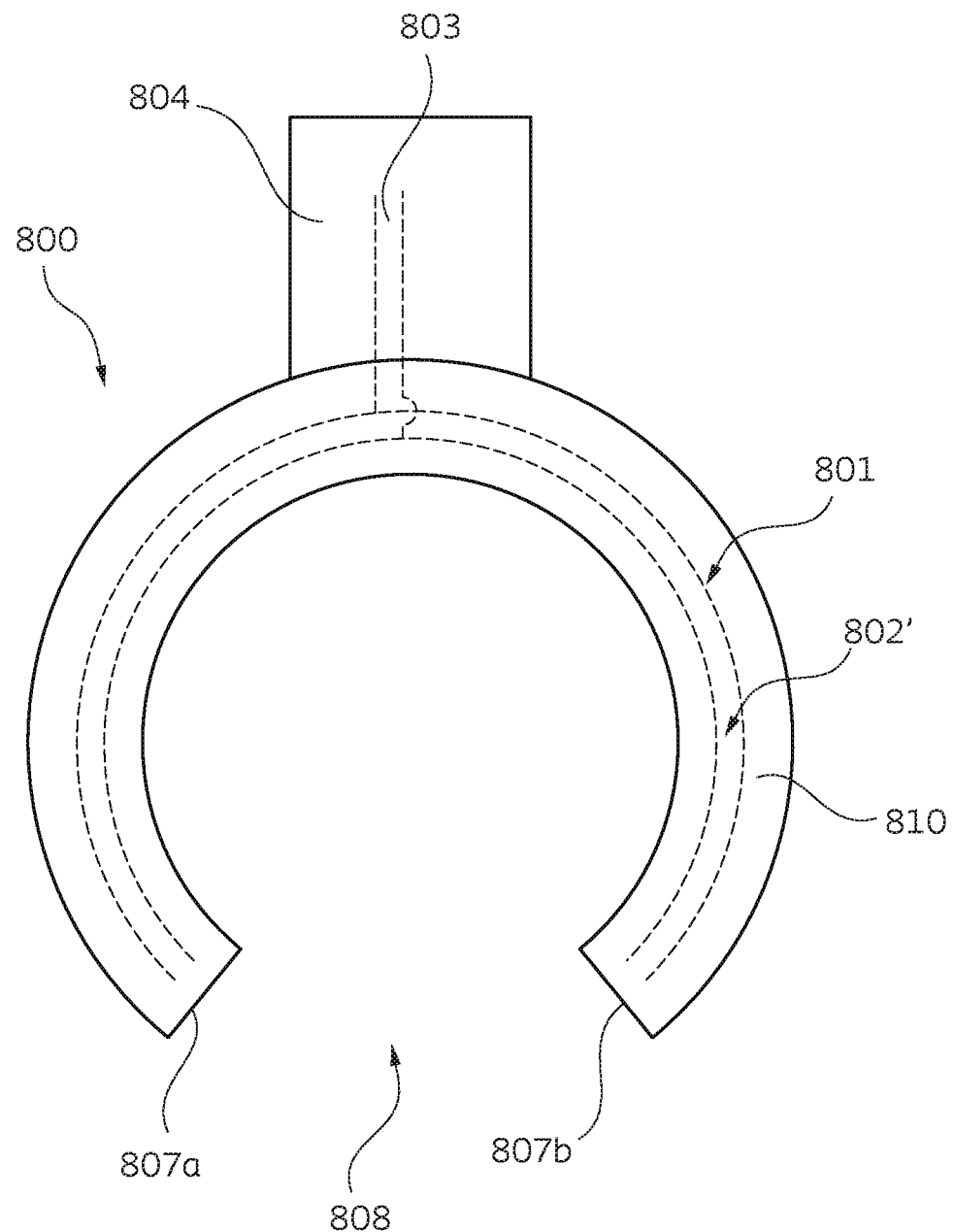
FIG. 11 illustrates a top view of an embodiment of a sensor patch.

FIG. 11 illustrates a top view of a sensor patch 800 having a first set of electrodes 802' comprising a spatial layout 801, and an adhesive layer 810. The spatial layout 801 is sickle-shaped, such that a large slit/passage 808 is formed between two terminating ends 807a,807b of the spatial layout 801 of the electrodes 802'. The large slit 808 creates a passage from the surroundings into a partly-encapsulated through-going aperture 2. Thus, the sickle-shape can comprise the curvature of a ring for a limited angle space, i.e. from 0 to an angle being less than 360 degrees, e.g. less than 270 degrees. The spatial layout 801 can be considered having the shape of a crescent. For example, the spatial layout 801 extends from 0 to 270 degrees, or from 0 to 180 degrees, or from 0 to 135 degrees, or from 0 to 90 degrees. The adhesive layer 810 corresponds in shape to the spatial layout 801, including a rim zone on each side of the spatial layout 801, and including where the electrodes 802' terminate in the ends 807a,807b. A monitor interface 803 and a neck portion 804 is provided on a segment of the outer periphery 812 of the adhesive layer 810. The position of the neck portion 804 relative to the outer periphery 812 may vary. For example, the neck portion 804 can flush with one of the ends 807a, 807b, or it can be arranged equidistant each of the two ends 807a,807b, as illustrated. The provision of a large slit/passage 808 in the sensor patch 800 allows for easy attachment to a generic base plate. The sensor patch 800 provides sensing abilities in regions of the spatial layout 801. Thus, the coverage of the sensor patch 800 is limited to the regions of the spatial layout 801. However, such limited coverage can be sufficient for users experiencing a tendency to leakage in certain regions of the peristomal skin area. Thus, the user may consider a sickle-shaped sensor patch 800 if he/she can orient the sensor patch 800 on his/her generic base plate relative to a region having an increased tendency to leakage and/or detachment.

Whereas certain spatial layouts of the one or more electrodes have been illustrated in the various embodiments, the invention should not be thought of as being limited to these spatial layouts. Instead, the certain spatial layouts are meant to illustrate how the adhesive layer corresponds in shape to a given spatial layout of the one or more electrodes. For example, the provision of a common ground (discussed in FIGS. 1C, 3B, and 6B) may be applied to all embodiments of the spatial layout, such that sensor(s) are formed between the one or more live electrodes and the ground. Likewise, the provision of the monitor interface is not to limit the invention. Instead, the monitor interface is included in certain embodiments to illustrate how the adhesive layer corresponds in shape to the spatial layout of the one or more electrodes. In other embodiments, the monitor interface has been omitted, and in these embodiments, it is envisioned that the electrodes can terminate in such a monitor interface arranged at any point on the outer periphery of the adhesive layer.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

The invention claimed is:

1. A sensor patch for attachment to a base plate of an ostomy appliance, the sensor patch comprising:
    a distal surface adapted for attachment to an inner portion of an adhesive surface of the base plate;
    a proximal surface adapted for attachment to a skin surface of a user, thereby adhering the sensor patch between the skin surface of the user and the base plate of the ostomy appliance;
    an outer contour;
    one or more electrodes comprising a spatial layout, and
    a planar adhesive layer having a proximal side and a distal side and comprising a first spatial shape, wherein the one or more electrodes are arranged on the distal side of the adhesive layer and wherein the first spatial shape of the adhesive layer generally corresponds to the spatial layout of the one or more electrodes, wherein the sensor patch is sized to expose an outer portion of the adhesive surface of the base plate, thereby enabling adhesion by the outer portion of the adhesive surface of the base plate to the skin surface of the user, in addition to adhesion by the proximal surface of the sensor patch.

2. The sensor patch according to claim 1, wherein the spatial layout of the one or more electrodes is substantially planar.

3. The sensor patch according to claim 1, wherein the adhesive layer comprises an outer periphery defining the outer contour of the sensor patch.

4. The sensor patch according to claim 3, wherein the adhesive layer comprises an inner periphery defining a stomal opening.

5. The sensor patch according to claim 4, wherein the diameter of the stomal opening is at least 40 mm.

6. The sensor patch according to claim 4, wherein the outer periphery and the inner periphery of the adhesive layer are concentric circles.

7. The sensor patch according to claim 6, wherein a width of the adhesive layer as measured from the inner periphery to the outer periphery is less than 25 mm.

8. The sensor patch according to claim 1, wherein the proximal side of the adhesive layer comprises a proximal surface having a first area being smaller than a second area defined by the outer contour of the sensor patch.

9. The sensor patch according to claim 8, wherein the proximal surface of the adhesive layer is the proximal surface of the sensor patch.

10. The sensor patch according to claim 1, wherein a minimum distance from at least one electrode of the one or more electrodes to a periphery of the adhesive layer is 4 mm.

11. The sensor patch according to claim 1, wherein a maximum distance from at least one electrode of the one or more electrodes to a periphery of the adhesive layer is 10 mm.

12. The sensor patch according to claim 1, wherein the one or more electrodes is/are provided in a sensor assembly comprising a support layer.

13. The sensor patch according to claim 12, wherein the support layer comprises a second spatial shape being identical to the first spatial shape of the adhesive layer.

14. The sensor patch according to claim 1, wherein the adhesive layer comprises two or more through-going openings extending from the proximal side of the adhesive layer to the distal side of the adhesive layer.

15. The sensor patch according to claim 1, wherein the sensor patch comprises two or more electrodes including a first electrode and a second electrode for forming a first sensor.

16. The sensor patch according to claim 15, wherein the spatial layout of the two or more electrodes comprises an outer ring of one or more electrodes and an inner ring of one or more electrodes, the outer ring encircling the inner ring.

17. The sensor patch according to claim 1, wherein the spatial layout of the one or more electrodes is a ring having an inner diameter of not more than 40 mm.

18. The sensor patch according to claim 1, wherein the spatial layout of the one or more electrodes is a ring having an inner diameter of at least 40 mm.

19. The sensor patch according to claim 1, wherein the sensor patch further comprises a release liner arranged on the proximal surface of the sensor patch.

20. The sensor patch according to claim 1, wherein the spatial layout of the one or more electrodes has a conforming geometrical feature to the first spatial shape of the adhesive layer.

* * * * *